US010093747B2

(12) United States Patent
Kurihara et al.

(10) Patent No.: US 10,093,747 B2
(45) Date of Patent: *Oct. 9, 2018

(54) METHOD FOR PRODUCTION SUGAR LIQUID

(71) Applicant: Toray Industries, Inc., Tokyo (JP)

(72) Inventors: Hiroyuki Kurihara, Kamakura (JP); Atsushi Minamino, Kamakura (JP); Masateru Ito, Kamakura (JP); Hideki Sawai, Kamakura (JP); Masayuki Hanakawa, Otsu (JP); Shin-ichi Minegishi, Otsu (JP); Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 628 days.

This patent is subject to a terminal disclaimer.

(21) Appl. No.: 14/288,742

(22) Filed: May 28, 2014

(65) Prior Publication Data

US 2014/0287461 A1 Sep. 25, 2014

Related U.S. Application Data

(62) Division of application No. 13/133,788, filed as application No. PCT/JP2009/070512 on Dec. 8, 2009, now Pat. No. 8,765,405.

(30) Foreign Application Priority Data

Dec. 9, 2008 (JP) ................................. 2008-313167
Sep. 4, 2009 (JP) ................................. 2009-204973

(51) Int. Cl.
| | | |
|---|---|---|
| C08B 1/00 | (2006.01) | |
| C12P 13/00 | (2006.01) | |
| B01D 61/02 | (2006.01) | |
| C12N 1/38 | (2006.01) | |
| C12P 7/10 | (2006.01) | |
| C12P 7/46 | (2006.01) | |
| C12P 7/56 | (2006.01) | |
| C12P 19/02 | (2006.01) | |
| C12P 19/14 | (2006.01) | |
| C13B 20/16 | (2011.01) | |
| C13K 1/02 | (2006.01) | |
| C13K 13/00 | (2006.01) | |
| C13K 1/04 | (2006.01) | |

(52) U.S. Cl.
CPC ............ *C08B 1/003* (2013.01); *B01D 61/022* (2013.01); *B01D 61/025* (2013.01); *B01D 61/027* (2013.01); *C12N 1/38* (2013.01); *C12P 7/10* (2013.01); *C12P 7/46* (2013.01); *C12P 7/56* (2013.01); *C12P 13/001* (2013.01); *C12P 19/02* (2013.01); *C12P 19/14* (2013.01); *C13B 20/165* (2013.01); *C13K 1/02* (2013.01); *C13K 1/04* (2013.01); *C13K 13/00* (2013.01); *C13K 13/002* (2013.01); *C12P 2203/00* (2013.01); *Y02E 50/16* (2013.01)

(58) Field of Classification Search
USPC ......................................................... 435/69.1
See application file for complete search history.

(56) References Cited

U.S. PATENT DOCUMENTS

| | | | |
|---|---|---|---|
| 6,409,841 B1 | 6/2002 | Lombard | |
| 7,077,953 B2 | 7/2006 | Ranney | |
| 2002/0148791 A1* | 10/2002 | DeFrees | ............... B01D 61/022 210/767 |
| 2005/0173319 A1* | 8/2005 | Fritze | ................... B01D 35/153 210/137 |

FOREIGN PATENT DOCUMENTS

| | | |
|---|---|---|
| BR | PI 0513398-0 A | 5/2008 |
| CN | 1594339 A | 3/1995 |
| CN | 100365006 C | 1/2008 |
| CN | 101138413 A | 3/2008 |
| JP | 62-201606 A | 9/1987 |
| JP | 01-058960 B2 | 12/1989 |
| JP | 11-506934 T | 6/1999 |
| JP | 3041380 B2 | 5/2000 |
| JP | 2001-095594 A | 4/2001 |
| JP | 2001-095597 A | 4/2001 |
| JP | 2001-511418 T | 8/2001 |
| JP | 2003-212888 A | 7/2003 |
| JP | 2004-187650 A | 7/2004 |
| JP | 2004-222569 A | 8/2004 |
| JP | 2005-229821 A | 9/2005 |
| JP | 2005-270056 A | 10/2005 |
| JP | 2001-000801 A | 1/2007 |
| JP | 2007-000801 A | 1/2007 |
| JP | 2007-074939 A | 3/2007 |
| JP | 2008-054472 A | 3/2008 |
| JP | 2008-099667 | 5/2008 |
| JP | 2008-100220 A | 5/2008 |
| JP | 2008-161125 A | 7/2008 |
| JP | 2008-535664 T | 9/2008 |
| JP | 2009-298721 A | 12/2009 |

(Continued)

OTHER PUBLICATIONS

Liu, Shijie et al. Membrane Filtration: Concentration & Purification of Hydrolyzates from Biomass. Journal of Biobased Materials and Bioenergy. vol. 2, pp. 121-134. 2008.*

(Continued)

*Primary Examiner* — Scott Long
*Assistant Examiner* — Nghi V Nguyen
(74) *Attorney, Agent, or Firm* — DLA Piper LLP (US)

(57) ABSTRACT

A method of producing a sugar liquid using a cellulose-containing biomass as a raw material includes (a) hydrolyzing a cellulose-containing biomass to produce an aqueous sugar solution and (b) filtering the obtained aqueous sugar solution through a reverse osmosis membrane to collect a purified sugar liquid from a feed side, while removing fermentation-inhibiting substances from a permeate side.

13 Claims, 4 Drawing Sheets

Specification includes a Sequence Listing.

(56) References Cited

FOREIGN PATENT DOCUMENTS

| RU | 2159816 C2 | 11/2000 |
|---|---|---|
| WO | 2002/053781 A1 | 7/2002 |
| WO | 2006/007691 A1 | 1/2006 |
| WO | 2007/097260 A1 | 8/2007 |
| WO | 2009/110374 A1 | 9/2009 |

OTHER PUBLICATIONS

Jarusutthirak, Chalor et al. Factors affecting nanofiltration performances in natural organic matter rejection and flux decline. Separation and Purification Technology 58 (2007). pp. 68-75.*

Kim, Hyun-Ah et al. Comparison of Initial Filtration Resistance by Pretreatment Processes in the Nanofiltration for Drinking Water Treatment. Separation and Purification Technology 56 (2007). pp. 354-362.*

Duarte, GV et al. Polymer induced flocculation and separation of particulates from extracts of lignocellulosic materials. Bioresource Technology 101 (2010). pp. 8526-8534.*

Liu (Membrane Filtration: Concentration & Purification of Hydrolyzates from Biomass, 2008).*

Duarte (Polymer induced flocculation and separation of particulates from extracts of lignocellulosic materials, 2009).*

M. Furuichi, "Use of Membrane Separation Technologies in Process for Producing Alcohol from Biomass," Bioscience & Industry, 1989, vol. 47, pp. 951-954 and English translation pp. 1-8.

M.M. Shah et al., "Simultaneous Saccharification and Extractive Fermentation for Acetone/Butanol Production from Pretreated Hardwood," Applied Biochemistry and Biotechnology, 1992, vol. 34, No. 35, pp. 557-568.

Hokkaido University Collection of Scholarly and Academic Papers: HUSCAP, (Eisei Kogaku Symposium), 1997, vol. 5, pp. 161-165.

Naoki Ohta et al., "A Study of Membrane Selection in Nanofiltration Methods," Proceedings of Sanitary Engineering Symposium, Hokkaido University, Nov. 1, 1997, vol. 5, pp. 161-165.

T. Inoue, "Super Ultralow Pressure Nanofiltration (NF) Membrane," Bunri Gijutsu, 2001, vol. 31, pp. 322-325 and English translation.

R. Millati et al., "Effect of pH, Time and Temperature of Overliming on Detoxification of Dilute-Acid Hydrolyzates for Fermentation by *Saccaharomyces cerevisiae*," Process Biochemistry, 2002, vol. 38, pp. 515-522.

A. Aden et al., :Lignocellulosic Biomass to Ethanol Process Design and Economics Utilizing Co-Current Dilute Acid Prehydrolysis and Enzymatic Hydrolysis for Corn Stover, National Renewable Energy Laboratory, Jun. 2002, Cover, Table of Contents, pp. 1-88 and Appendixes 1-I.

Christopher Bellona et al., "Factors affecting the rejection of organic solutes during NF/RO treatment—a literature review," Water Research, 2004, vol. 38, pp. 2795-2809.

QP Yuan et al., "Pilot-plant production of xylo-oligosaccharides from corncob by steaming, enzymatic hydrolysis and nanofiltration," Journal of Chemical Technology and Biotechnology, (online) 2004, vol. 79, pp. 1073-1079.

G.S. Murthy et al., "Concentration of xylose reaction liquor by nanofiltration for the production of xylitol sugar alcohol," Separation and Purification Technology, 2004, vol. 44, pp. 221-228.

Abdulgader A. Maghrabi et al., "Effect of High Feed Temperature on Nanofiltration and RO Membrane Performance," Technical Report No. 3807/03016, Saline Water Desalination Research Institute, Saline Water Conversion Corporation, May 2005.

Hyun-Ah Kim et al., "Comparison of Initial Filtration Resistance by Pretreatment Processes in the NF for Drinking Water Treatment," Elsevier, Separation Purification Technology, 2007, vol. 56, pp. 354-362.

Chalor Jarusutthirak et al., "Factors affecting nanofiltration performances in natural organic matter rejection and flux decline," Elsevier, Separation Purification Technology, 2007, vol. 58, pp. 68-75.

Shinsuke Sakai et al., "Effect of Lignocellulose-Derived Inhibitors on Growth of and Ethanol Production by Growth-Arrested *Corynebacterium glutamicum* R," Applied and Environmental Microbiology, Apr. 2007, pp. 2349-2353.

S. Liu et al., "Membrane Filtration: Concentration and Purification of Hydrolyzates from Biomass," Journal of Biobased Materials and Bioenergy, 2008, vol. 2, pp. 121-134.

English translation of Russian Search Report dated Oct. 31, 2013.

Supplementary European Search Report dated Jan. 23, 2015 of corresponding European Application No. 14003242.6.

Baker, R., "Reverse Osmosis," *Membrane Technology and Applications*, Second Edition, John Wiley & Sons, Jan. 1, 2004, pp. 191-235.

Brazilian Official Action dated Jan. 16, 2018 in corresponding Brazilian Patent Application No. PI 0917617-9.

* cited by examiner

Microfiltration membrane before treatment    Microfiltration membrane after treatment C (Carbon)   Si (Silicon)   O (Oxygen)

SEQUENCE LISTING

```
<160> NUMBER OF SEQ ID NOS: 20

<210> SEQ ID NO 1
<211> LENGTH: 26
<212> TYPE: DNA
<213> ORGANISM: Artificial
<220> FEATURE:
<223> OTHER INFORMATION: Description of Artificial Sequence: primer

<400> SEQUENCE: 1
ctcgagatgg caactctaaa ggatca                                         26
```

<210> SEQ ID NO 2
<211> LENGTH: 28
<212> TYPE: DNA
<213> ORGANISM: Artificial
<220> FEATURE:
<223> OTHER INFORMATION: Description of Artificial Sequence: primer

<400> SEQUENCE: 2
gcggccgctt aaaattgcag ctcctttt              28

<210> SEQ ID NO 3
<211> LENGTH: 999
<212> TYPE: DNA
<213> ORGANISM: Homo sapiens

<400> SEQUENCE: 3
atggcaactc taaaggatca gctgatttat aatcttctaa aggaagaaca gacccccag      60
aataagatta cagttgttgg ggttggtgct gttggcatgg cctgtgccat cagtatctta    120
atgaaggact tggcagatga acttgctctt gttgatgtca tcgaagacaa attgaaggga    180
gagatgatgg atctccaaca tggcagcctt ttccttagaa caccaaagat tgtctctggc    240
aaagactata atgtaactgc aaactccaag ctggtcatta tcacggctgg ggcacgtcag    300
caagagggag aaagccgtct taatttggtc cagcgtaacg tgaacatatt taaattcatc    360
attcctaatg ttgtaaaata cagcccgaac tgcaagttgc ttattgtttc aaatccagtg    420
gatatcttga cctacgtggc ttggaagata agtggttttc ccaaaaaccg tgttattgga    480
agtggttgca atctggattc agcccgattc cgttacctga tgggggaaag gctgggagtt    540
cacccattaa gctgtcatgg gtgggtcctt ggggaacatg gagattccag tgtgcctgta    600
tggagtggaa tgaatgttgc tggtgtctct ctgaagactc tgcacccaga tttagggact    660
gataaagata aggaacagtg aaagaggtt cacaagcagg tggttgagag tgcttatgag    720
gtgatcaaac tcaaaggcta cacatcctgg gctattggac tctctgtagc agatttggca    780
gagagtataa tgaagaatct taggcgggtg cacccagttt ccaccatgat taagggtctt    840
tacggaataa aggatgatgt cttccttagt gttccttgca ttttgggaca gaatggaatc    900
tcagaccttg tgaaggtgac tctgacttct gaggaagagg cccgtttgaa gaagagtgca    960
gatacacttt gggggatcca aaaggagctg caattttaa                         999

<210> SEQ ID NO 4
<211> LENGTH: 80
<212> TYPE: DNA
<213> ORGANISM: Artificial
<220> FEATURE:
<223> OTHER INFORMATION: Description of Artificial Sequence: primer

<400> SEQUENCE: 4
tctcaattat tattttctac tcataacctc acgcaaaata acacagtcaa atcaatcaaa     60
atggcaactc taaaggatca                                                80

<210> SEQ ID NO 5
<211> LENGTH: 20
<212> TYPE: DNA
<213> ORGANISM: Artificial
<220> FEATURE:
<223> OTHER INFORMATION: Description of Artificial Sequence: primer

<400> SEQUENCE: 5
aggcgtatca cgaggccctt              20

```
<210> SEQ ID NO 6
<211> LENGTH: 60
<212> TYPE: DNA
<213> ORGANISM: Artificial
<220> FEATURE:
<223> OTHER INFORMATION: Description of Artificial Sequence: primer

<400> SEQUENCE: 6
gaattaattc ttgaagacga aagggcctcg tgatacgcct agattgtact gagagtgcac    60

<210> SEQ ID NO 7
<211> LENGTH: 80
<212> TYPE: DNA
<213> ORGANISM: Artificial
<220> FEATURE:
<223> OTHER INFORMATION: Description of Artificial Sequence: primer

<400> SEQUENCE: 7 tattttttcgt tacataaaaa tgcttataaa actttaacta ataattagag attaaatcgc    60
ctgtgcggta tttcacaccg                                                80

<210> SEQ ID NO 8
<211> LENGTH: 25
<212> TYPE: DNA
<213> ORGANISM: Artificial
<220> FEATURE:
<223> OTHER INFORMATION: Description of Artificial Sequence: primer

<400> SEQUENCE: 8
caaatatcgt ttgaatattt ttccg                                          25

<210> SEQ ID NO 9
<211> LENGTH: 20
<212> TYPE: DNA
<213> ORGANISM: Artificial
<220> FEATURE:
<223> OTHER INFORMATION: Description of Artificial Sequence: primer

<400> SEQUENCE: 9
aatccagatt gcaaccactt                                                20

<210> SEQ ID NO 10
<211> LENGTH: 30
<212> TYPE: DNA
<213> ORGANISM: Artificial
<220> FEATURE:
<223> OTHER INFORMATION: Description of Artificial Sequence: primer

<400> SEQUENCE: 10
atgcaagctt cagcggggca tcgcagatca                                     30

<210> SEQ ID NO 11
<211> LENGTH: 30
<212> TYPE: DNA
<213> ORGANISM: Artificial
<220> FEATURE:
<223> OTHER INFORMATION: Description of Artificial Sequence: primer

<400> SEQUENCE: 11
atgcaagctt atattccacc agctatttgt                                     30

<210> SEQ ID NO 12
<211> LENGTH: 30
<212> TYPE: DNA
<213> ORGANISM: Artificial
```

<220> FEATURE:
<223> OTHER INFORMATION: Description of Artificial Sequence: primer

<400> SEQUENCE: 12
atgcaagctt atgaacgtta ttgcaatatt                                    30

<210> SEQ ID NO 13
<211> LENGTH: 30
<212> TYPE: DNA
<213> ORGANISM: Artificial
<220> FEATURE:
<223> OTHER INFORMATION: Description of Artificial Sequence: primer

<400> SEQUENCE: 13
atgctctaga ttattttttg ctttcttctt                                    30

<210> SEQ ID NO 14
<211> LENGTH: 30
<212> TYPE: DNA
<213> ORGANISM: Artificial
<220> FEATURE:
<223> OTHER INFORMATION: Description of Artificial Sequence: primer

<400> SEQUENCE: 14
atgcggatcc tgtgtaggct ggagctgctt                                    30

<210> SEQ ID NO 15
<211> LENGTH: 30
<212> TYPE: DNA
<213> ORGANISM: Artificial
<220> FEATURE:
<223> OTHER INFORMATION: Description of Artificial Sequence: primer

<400> SEQUENCE: 15
atgcgagctc catatgaata tcctccttag                                    30

<210> SEQ ID NO 16
<211> LENGTH: 17
<212> TYPE: DNA
<213> ORGANISM: Artificial
<220> FEATURE:
<223> OTHER INFORMATION: Description of Artificial Sequence: primer

<400> SEQUENCE: 16
caggaaacag ctatgac                                                  17

<210> SEQ ID NO 17
<211> LENGTH: 70
<212> TYPE: DNA
<213> ORGANISM: Artificial
<220> FEATURE:
<223> OTHER INFORMATION: Description of Artificial Sequence: primer

<400> SEQUENCE: 17
cattttgtcc catgtgttgg gaggggcctt ttttacctgg agatatgact cagcggggca   60
tcgcagatca                                                          70

<210> SEQ ID NO 18
<211> LENGTH: 70
<212> TYPE: DNA
<213> ORGANISM: Artificial
<220> FEATURE:
<223> OTHER INFORMATION: Description of Artificial Sequence: primer

```
<400> SEQUENCE: 18
cttatgagca aaaagggaa gtggcaagcc acttcccttg tacgagctaa aaacgacggc      60
cagtgaattc                                                           70

<210> SEQ ID NO 19
<211> LENGTH: 20
<212> TYPE: DNA
<213> ORGANISM: Artificial
<220> FEATURE:
<223> OTHER INFORMATION: Description of Artificial Sequence: primer

<400> SEQUENCE: 19
accgcgtcta acgcacatta                                                20

<210> SEQ ID NO 20
<211> LENGTH: 20
<212> TYPE: DNA
<213> ORGANISM: Artificial
<220> FEATURE:
<223> OTHER INFORMATION: Description of Artificial Sequence: primer

<400> SEQUENCE: 20
cacgatatag tatatcgcgc                                                20
```

METHOD FOR PRODUCTION SUGAR LIQUID

TECHNICAL FIELD

This disclosure relates to methods of producing a sugar liquid from a cellulose-containing biomass.

BACKGROUND

The process of fermentation production of chemical products using sugars as raw materials has been used for producing various industrial materials. At present, as the sugars to be used as fermentation feedstocks, those derived from food materials such as sugar cane, starch and sugar beet are industrially used. However, in view of the fact that rise in the prices of food materials is expected due to future increase in the world population, or in an ethical view of the fact that sugars as industrial materials may compete with sugars for food, a process for efficiently producing a sugar liquid from a renewable nonfood resource, that is, cellulose-containing biomass, or a process for efficiently converting an obtained sugar liquid as a fermentation feedstock to an industrial material needs to be constructed in the future.

Examples of disclosed methods for producing a sugar liquid from a cellulose-containing biomass include methods for producing sugar liquids using sulfuric acid, such as methods for producing sugar liquids by acid hydrolysis of cellulose and hemicellulose using concentrated sulfuric acid (Japanese Translated PCT Patent Application Laid-open No. 11-506934 and JP 2005-229821 A) and a method wherein a cellulose-containing biomass is subjected to hydrolysis treatment using dilute sulfuric acid and then enzymatically treated with cellulase and the like to produce a sugar liquid (A. Aden et al., "Lignocellulosic Biomass to Ethanol Process Design and Economics Utilizing Co-Current Dilute Acid Prehydrolysis and Enzymatic Hydrolysis for Corn Stover," NREL Technical Report (2002)).

Further, examples of disclosed methods in which acids are not used include a method wherein a cellulose-containing biomass is hydrolyzed using subcritical water at about 250 to 500° C. to produce a sugar liquid (JP 2003-212888 A), a method wherein a cellulose-containing biomass is subjected to subcritical water treatment and then enzymatically treated to produce a sugar liquid (JP 2001-95597 A), and a method wherein a cellulose-containing biomass is subjected to hydrolysis treatment with pressurized hot water at 240° C. to 280° C. and then enzymatically treated to produce a sugar liquid (JP 3041380 B).

However, during the hydrolysis of a cellulose-containing biomass, at the same time with decomposition of the cellulose or hemicellulose component or the like, decomposition reaction of produced sugars such as glucose and xylose proceeds, and by-products such as furan compounds including furfural and hydroxymethylfurfural; and organic acids including formic acid, acetic acid and levulinic acid; are produced, which have been problematic. Further, since a cellulose-containing biomass contains lignin components, which are aromatic polymers, the lignin components are decomposed during the acid treatment step to produce low molecular aromatic compounds such as phenols as by-products at the same time. These compounds have inhibitory actions during the fermentation step using a microorganism and cause inhibition of the growth of the microorganism, leading to decrease in the yield of the fermentation product. Therefore, these compounds are called fermentation-inhibiting substances and have been seriously problematic when a cellulose-containing biomass sugar liquid was used as a fermentation feedstock.

Examples of the method, which has been disclosed, for removing such fermentation-inhibiting substances during the sugar liquid-producing process include the method called overliming (M. Alfred et al., "Effect of pH, time and temperature of overliming on detoxification of dilute-acid hydrolyzates for fermentation by *Saccaromyces cerevisiase*," Process Biochemistry, 38, 515-522 (2002)). In this method, during a step of neutralizing an acid-treated cellulose or saccharified liquid by addition of lime, the liquid is maintained while being heated to about 60° C. for a certain period, to remove fermentation-inhibiting substances such as furfural and HMF together with the gypsum component. However, overliming has only a small effect of removing organic acids such as formic acid, acetic acid and levulinic acid, which has been problematic.

Further, as another method for removing fermentation-inhibiting substances, a method wherein water vapor is blown into a sugar liquid prepared from a cellulose-containing biomass to remove fermentation-inhibiting substances by evaporation has been disclosed (JP 2004-187650 A). However, since such a method by evaporative removal is dependent on the boiling points of the fermentation-inhibiting substances, the removal efficiencies of fermentation-inhibiting substances such as organic acids having low boiling points are especially low, so that a large amount of energy is required to obtain sufficient removal efficiencies, which has been problematic.

There is also a method wherein fermentation-inhibiting substances are removed by ion exchange (Japanese Translated PCT Patent Application Laid-open No. 2001-511418), but it has been problematic in view of the cost. Further, there is a method wherein adsorptive removal is carried out using a wood-based carbide, that is, active carbon or the like, but the subjects to be removed are limited to hydrophobic compounds, which has been problematic (JP 2005-270056 A).

SUMMARY

We thus provide a method wherein fermentation-inhibiting substances produced in the step of producing a sugar from a cellulose-containing biomass are removed during the step of producing a sugar liquid, and a method for producing a purified sugar liquid containing only a very small amount of fermentation-inhibiting substances, are provided.

In particular, we discovered that, by allowing a sugar liquid to pass through a nanofiltration membrane and/or reverse osmosis membrane during a step of producing a sugar from a cellulose-containing biomass, the sugar to be used as a fermentation feedstock and fermentation-inhibiting substances can be separated, fermentation-inhibiting substances can be removed from a sugar liquid. This is constituted as follows:

[1] A method of producing a sugar liquid using a cellulose-containing biomass as a raw material, the method including:
  (1) a step of hydrolyzing a cellulose-containing biomass to produce an aqueous sugar solution; and
  (2) a step of filtering the obtained aqueous sugar solution through a nanofiltration membrane and/or reverse osmosis membrane to collect a purified sugar liquid from the feed side, while removing fermentation-inhibiting substances from the permeate side.

[2] The method according to [1], wherein the pH of the aqueous sugar solution in the Step (2) is adjusted to 1 to 5.

[3] The method according to [1] or [2], wherein the fermentation-inhibiting substances comprise one or more selected from the group consisting of organic acids, furan compounds and phenolic compounds.

[4] The method according to [3], wherein the organic acid is formic acid or acetic acid.

[5] The method according to [3], wherein the furan compound is hydroxymethylfurfural or furfural.

[6] The method according to [3], wherein the phenolic compound is vanillin, acetovanillin or syringic acid.

[7] The method according to any one of [1] to [6], wherein the purified sugar liquid in the Step (2) is a sugar liquid containing a monosaccharide as major component.

[8] The method according to any one of [1] to [7], wherein the aqueous sugar solution obtained in the Step (1) is allowed to pass through a microfiltration membrane and/or ultrafiltration membrane to remove fine particles and macromolecular components before the treatment of the Step (2).

[9] The method according to any one of [1] to [8], wherein the temperature of the aqueous sugar solution in the Step (2) is adjusted to 1 to 15° C. and the solution is filtered through a nanofiltration membrane.

[10] The method according to any one of [1] to [8], wherein the temperature of the aqueous sugar solution in the Step (2) is adjusted to 40° C. to 80° C. and the solution is filtered through a reverse osmosis membrane.

[11] The method according to any one of [1] to [10], wherein the Step (2) is a step of filtering the aqueous sugar solution through a nanofiltration membrane and filtering the obtained filtrate through a reverse osmosis membrane.

[12] The method according to any one of [1] to [11], wherein the functional layer(s) of the nanofiltration membrane and/or reverse osmosis membrane in the Step (2) is/are polyamide.

[13] The method according to any one of [1] to [12], wherein the functional layer of the nanofiltration membrane in the Step (2) includes a cross-linked piperazine polyamide as a major component and further comprises a constituting component represented by Formula 1:

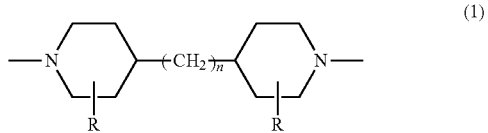

(1)

wherein R represents —H or —CH$_3$; and n represents an integer of 0 to 3.

[14] A method of producing a chemical product, which method uses, as a fermentation feedstock, a sugar liquid obtained by the method according to any one of [1] to [13].

Furan compounds such as furfural and HMF; organic acids such as acetic acid, formic acid and levulinic acid; and phenolic compounds such as vanillin; which are fermentation-inhibiting substances, can be comprehensively removed from an aqueous sugar solution derived from a cellulose-containing biomass, and, on the other hand, sugars such as glucose and xylose can be produced at high purity and at high yield. As a result, by using the obtained purified sugar liquid as a fermentation feedstock, the efficiency of fermentation production of various chemical products can be enhanced.

DETAILED DESCRIPTION

Figure 1:
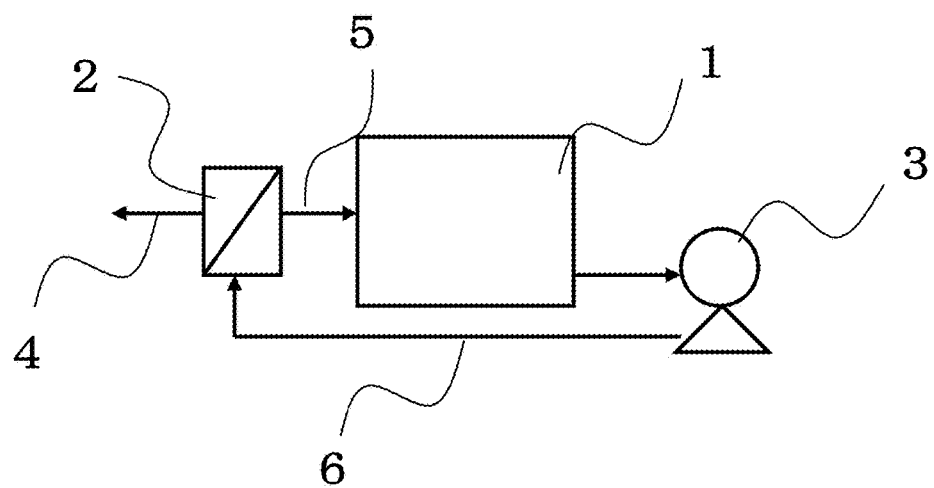
FIG. 1 shows an overview of a filtration device using a nanofiltration membrane/reverse osmosis membrane.

Our methods will now be described in more detail.

Examples of the cellulose-containing biomass used in the production method of the sugar liquid include herbaceous biomasses such as bagasse, switchgrass, corn stover, rice straw and wheat straw; and woody biomasses such as trees and waste building materials. These cellulose-containing biomasses contain cellulose or hemicellulose, which are polysaccharides produced by dehydration condensation of sugars. By hydrolyzing such polysaccharides, sugar liquids which may be used as fermentation feedstocks can be produced.

The sugar liquid means an aqueous sugar solution obtained by hydrolysis of a cellulose-containing biomass. Sugars are generally classified, based on the degree of polymerization of monosaccharides, into monosaccharides such as glucose and xylose, oligosaccharides produced by dehydration condensation of 2 to 9 monosaccharides, and polysaccharides produced by dehydration condensation of not less than 10 monosaccharides. The sugar liquid means a sugar liquid containing a monosaccharide(s) as a major component(s), and more particularly, the sugar liquid contains glucose or xylose as a major component. Further, the sugar liquid also contains oligosaccharides such as cellobiose; and monosaccharides such as arabinose and mannose, although their amounts are small. The term "containing a monosaccharide as a major component" means that a monosaccharide(s) constitute(s) not less than 80% by weight of the total weight of sugars such as monosaccharides, oligosaccharides and polysaccharides dissolved in water. Particular examples of the method for analyzing monosaccharides, oligosaccharides and polysaccharides dissolved in water include quantification by HPLC based on comparison with a standard sample. Concrete HPLC conditions are: no use of a reaction liquid; use of Luna NH$_2$ (manufactured by Phenomenex, Inc.) as a column; mobile phase, ultrapure water:acetonitrile=25:75; flow rate, 0.6 mL/min.; measurement time, 45 min.; detection method, RI (differential refractive index); temperature, 30° C.

Step (1), which is a step of hydrolyzing a cellulose-containing biomass, in the method for producing a sugar liquid will now be described.

When a cellulose-containing biomass is subjected to hydrolysis, the cellulose-containing biomass may be used as it is, or may be subjected to a known treatment such as steaming, pulverization or blasting. By such a treatment, the efficiency of the hydrolysis can be enhanced.

The step of hydrolysis of the cellulose-containing biomass is not restricted, and particular examples thereof mainly include 6 methods, that is, the procedure A: a method using only an acid; the procedure B: a method wherein acid treatment is carried out, followed by usage of an enzyme; the procedure C; a method using only hydrothermal treatment; the procedure D: a method wherein hydrothermal treatment is carried out, followed by usage of an enzyme; the procedure E: a method wherein alkaline treatment is carried out, followed by usage of an enzyme; and the procedure F: a method wherein ammonia treatment is carried out, followed by usage of an enzyme.

In the procedure A, an acid is used for the hydrolysis of a cellulose-containing biomass. Examples of the acid to be used include sulfuric acid, nitric acid and hydrochloric acid, and sulfuric acid is preferably used.

The concentration of the acid is not restricted, and an acid at a concentration of 0.1 to 99% by weight may be used. In cases where the concentration of the acid is 0.1 to 15% by weight, preferably 0.5 to 5% by weight, the reaction temperature is set within the range of 100 to 300° C., preferably 120 to 250° C., and the reaction time is set within the range of 1 second to 60 minutes. The number of times of the treatment is not restricted, and 1 or more times of the above-described treatment may be carried out. In particular, in cases where the above-described treatment is carried out 2 or more times, the conditions for the first treatment may be different from those for the second and later treatments.

Further, in cases where the concentration of the acid is 15 to 95% by weight, preferably 60 to 90% by weight, the reaction temperature is set within the range of 10 to 100° C., and the reaction time is set within the range of 1 second to 60 minutes.

The number of times of the acid treatment is not restricted, and 1 or more times of the above-described treatment may be carried out. In particular, in cases where the above-described treatment is carried out 2 or more times, the conditions for the first treatment may be different from those for the second and later treatments.

Since the hydrolysate obtained by the acid treatment contains acids such as sulfuric acid, it needs to be neutralized to be used as a fermentation feedstock. The neutralization may be carried out either for the aqueous acid solution prepared by removal of the solid contents from the hydrolysate or in the state in which the solid contents are contained. The alkaline reagent to be used for the neutralization is not restricted, and preferably a monovalent alkaline reagent. In cases where both the acid and alkaline components are salts having valencies of 2 or more during the Step (2), these do not pass through the nanofiltration membrane, and the salts precipitate in the liquid during the process of concentration of the liquid, which may cause fouling of the membrane.

In cases where a monovalent alkali is used, examples of the alkali include, but are not limited to, ammonia, sodium hydroxide and potassium hydroxide.

In cases where an alkaline reagent having a valency of 2 or more is used, it is necessary to reduce the amounts of the acid and the alkali, or to employ a mechanism for removal of precipitates during the Step (2) to avoid precipitation of salts during the Step (2). In cases where an alkali having a valency of 2 or more is used, the alkali is preferably calcium hydroxide in view of the cost. Since, in cases where calcium hydroxide is used, the gypsum component is produced by neutralization, the gypsum needs to be removed by solid-liquid separation. Examples of the method of solid-liquid separation include, but are not limited to, centrifugation and membrane separation, and the gypsum may also be removed by carrying out plural types of separation steps.

In general, in hydrolysis using an acid, hydrolysis first occurs in the hemicellulose component having a low crystallinity, which is followed by degradation of the cellulose component having a high crystallinity. Therefore, it is possible, by using an acid, to obtain a liquid containing a large amount of xylose derived from hemicellulose. Further, in the acid treatment, by subjecting the biomass solid contents after the treatment to a reaction under a higher pressure at a higher temperature than in the above treatment, the cellulose component having a higher crystallinity can be decomposed to obtain a liquid containing a large amount of glucose derived from cellulose. By setting the two-stage step of hydrolysis, conditions for the hydrolysis which are suitable for hemicellulose and cellulose can be set, and the decomposition efficiency and the sugar yield can be enhanced. Further, by keeping the sugar liquid obtained under the first decomposition conditions and the sugar liquid obtained under the second decomposition conditions separate from each other, two types of sugar liquids having different ratios of monosaccharides contained in the hydrolysates can be produced. That is, it is also possible to separate the sugar liquid obtained under the first decomposition conditions as a sugar liquid containing xylose as a major component, and the sugar liquid obtained under the second decomposition conditions as a sugar liquid containing glucose as a major component. By separating the monosaccharide components contained in the sugar liquid as described above, the fermentation can be carried out separately as fermentation using xylose in the sugar liquid as a fermentation feedstock and as fermentation using glucose in the sugar liquid as a fermentation feedstock, wherein microorganism species which are most suitable for the respective types of fermentation can be selected and employed. It should be noted that the sugars derived from the both components may also be obtained at once without separating the hemicellulose component/cellulose component, by carrying out the high-pressure high-temperature treatment with an acid for a long time.

In the procedure B, the treated liquid obtained in the procedure A is further subjected to enzymatic hydrolysis of the cellulose-containing biomass. The concentration of the acid to be used in the procedure B is preferably 0.1 to 15% by weight, more preferably 0.5 to 5% by weight. The reaction temperature may be set within the range of 100 to 300° C., preferably 120 to 250° C. The reaction time may be set within the range of 1 second to 60 minutes. The number of times of the treatment is not restricted, and 1 or more times of the above-described treatment may be carried out. In particular, in cases where the above-described treatment is carried out 2 or more times, the conditions for the first treatment may be different from those for the second and later treatments.

Since the hydrolysate obtained by the acid treatment contains acids such as sulfuric acid, it needs to be neutralized to be further subjected to hydrolysis reaction with an enzyme or to be used as a fermentation feedstock. The neutralization may be carried out in the same manner as the neutralization in the procedure A.

The enzyme is not restricted as long as it is an enzyme having a cellulose decomposition activity, and commonly-used cellulases may be used. The enzyme is preferably a cellulase comprising an exo-type cellulase or endo-type cellulase having an activity to decompose crystalline cellulose. As such a cellulase, a cellulase produced by a microorganism belonging to a genus of *Trichoderma* is preferred. The genus of *Trichoderma* is a microorganism classified into filamentous fungi, and secretes a large amount of various cellulases extracellularly. The cellulase to be used herein is preferably a cellulase derived from *Trichoderma reesei*. Further, as an enzyme to be used for the hydrolysis, β-glucosidase, which is a cellobiose-decomposing enzyme, may be added to enhance the production efficiency of glucose, which β-glucosidase may also be used together with the above-mentioned cellulase for the hydrolysis. The β-glucosidase is not restricted, but preferably derived from a genus of *Aspergillus*. The hydrolysis reaction using such enzymes is preferably carried out at a pH of about 3 to 7, more preferably at a pH of about 5. The reaction temperature is preferably 40 to 70° C. Further, it is preferred to carry out solid-liquid separation after the completion of the enzymatic hydrolysis to remove the solid contents which have not been decomposed. Examples of the method of removal of the solid contents include centrifugation and membrane separation, but the method is not limited thereto. Further, such methods of solid-liquid separation may be used as a combination of a plurality of the methods.

In cases where the acid treatment is followed by enzymatic hydrolysis of the cellulose-containing biomass, it is preferred to carry out hydrolysis of hemicellulose having a low crystallinity by the acid treatment in the first hydrolysis, followed by carrying out hydrolysis of cellulose having a high crystallinity by using an enzyme in the second hydrolysis. By using the enzyme in the second hydrolysis, the step of hydrolysis of the cellulose-containing biomass can be allowed to proceed more efficiently. More particularly, in the first hydrolysis by an acid, hydrolysis of the hemicellulose component contained in the cellulose-containing biomass and partial decomposition of lignin mainly occur, and the resulting hydrolysate is separated into an acid solution and the solid contents containing cellulose. The solid contents containing cellulose is then hydrolyzed by addition of the enzyme. Since the separated/recovered solution in dilute sulfuric acid contains, as a major component, xylose, which is a pentose, an aqueous sugar solution can be isolated by neutralization of the acid solution. Further, from the hydrolysis reaction product of the solid contents containing cellulose, monosaccharide components containing glucose as a major component can be obtained. The aqueous sugar solution obtained by the neutralization may be mixed with the solid contents, followed by adding the enzyme to the resulting mixture to carry out hydrolysis.

In the procedure C, the acid is not particularly added, and water is added such that the concentration of the cellulose-containing biomass becomes 0.1 to 50% by weight, followed by treatment at a temperature of 100 to 400° C. for 1 second to 60 minutes. By carrying out the treatment under such a temperature condition, hydrolysis of cellulose and hemicellulose occurs. The number of times of the treatment is not restricted, and the treatment may be carried out 1 or more times. In particular, in cases where the above-described treatment is carried out 2 or more times, the conditions for the first treatment may be different from those for the second and later treatments.

In general, in hydrolysis employing hydrothermal treatment, hydrolysis first occurs in the hemicellulose component having a low crystallinity, which is followed by degradation of the cellulose component having a high crystallinity. Therefore, it is possible, by using hydrothermal treatment, to obtain a liquid containing a large amount of xylose derived from hemicellulose. Further, in the hydrothermal treatment, by subjecting the biomass solid contents after the treatment to a reaction under a higher pressure at a higher temperature than in the above treatment, the cellulose component having a higher crystallinity can be decomposed to obtain a liquid containing a large amount of glucose derived from cellulose. By setting the two-stage step of hydrolysis, conditions for the hydrolysis which are suitable for hemicellulose and cellulose can be set, and the decomposition efficiency and the sugar yield can be enhanced. Further, by keeping the sugar liquid obtained under the first decomposition conditions and the sugar liquid obtained under the second decomposition conditions separate from each other, two types of sugar liquids having different ratios of monosaccharides contained in the hydrolysates can be produced. That is, it is also possible to separate the sugar liquid obtained under the first decomposition conditions as a sugar liquid containing xylose as a major component, and the sugar liquid obtained under the second decomposition conditions as a sugar liquid containing glucose as a major component. By separating the monosaccharide components contained in the sugar liquid as described above, the fermentation can be carried out separately as fermentation using xylose in the sugar liquid as a fermentation feedstock and as fermentation using glucose in the sugar liquid as a fermentation feedstock, wherein microorganism species which are most suitable for the respective types of fermentation can be selected and used.

In the procedure D, the treated liquid obtained in the procedure C is further subjected to enzymatic hydrolysis of the cellulose-containing biomass.

The enzyme used may be the same as the one used in the procedure B. The conditions for the enzyme treatment may also be the same as those in the procedure B.

In cases where the hydrothermal treatment is followed by hydrolysis of the cellulose-containing biomass using an enzyme, it is preferred to carry out hydrolysis of hemicellulose having a low crystallinity by the hydrothermal treatment in the first hydrolysis, followed by carrying out hydrolysis of cellulose having a high crystallinity by using the enzyme in the second hydrolysis. By using the enzyme in the second hydrolysis, the step of hydrolysis of the cellulose-containing biomass can be allowed to proceed more efficiently. More particularly, in the first hydrolysis by the hydrothermal treatment, hydrolysis of the hemicellulose component contained in the cellulose-containing biomass and partial decomposition of lignin mainly occur, and the resulting hydrolysate is separated into an aqueous solution and the solid contents containing cellulose. The solid contents containing cellulose is then hydrolyzed by addition of an enzyme. The separated/recovered aqueous solution contains, as a major component, xylose, which is a pentose. Further, from the hydrolysis reaction product of the solid contents containing cellulose, monosaccharide components containing glucose as a major component can be obtained. The aqueous solution obtained by the hydrothermal treatment may be mixed with the solid contents, followed by adding an enzyme to the resulting mixture to carry out hydrolysis.

In the procedure E, the alkali to be used is more preferably sodium hydroxide or calcium hydroxide. These alkalis are added to the cellulose-containing biomass such that their concentrations are within the range of 0.1 to 60% by weight, and the treatment may be carried out at a temperature within the range of 100 to 200° C., preferably 110 to 180° C. The number of times of the treatment is not restricted, and 1 or more times of the above-described treatment may be carried out. In particular, in cases where the above-described treatment is carried out 2 or more times, the conditions for the first treatment may be different from those for the second and later treatments.

Since the treated product obtained by the alkaline treatment contains alkalis such as sodium hydroxide, it needs to be neutralized to be further subjected to hydrolysis reaction using an enzyme. The neutralization may be carried out either for the aqueous alkaline solution prepared by removal of the solid contents from the hydrolysate by solid-liquid separation, or in the state in which the solid contents are contained. The acid reagent to be used for the neutralization is not restricted, and preferably a monovalent acid reagent. In cases where both the acid and alkaline components are salts having valencies of 2 or more during the Step (2), these do not pass through the nanofiltration membrane, and the salts precipitate in the liquid during the process of concentration of the liquid, which may cause fouling of the membrane.

In cases where a monovalent acid is used, examples of the acid include, but are not limited to, nitric acid and hydrochloric acid.

In cases where an acid reagent having a valency of 2 or more is used, it is necessary to reduce the amounts of the acid and the alkali, or to employ a mechanism for removal of precipitates during the Step (2) to avoid precipitation of salts during the Step (2). In cases where an acid having a valency of 2 or more is used, the acid is preferably sulfuric acid or phosphoric acid. Since, in cases where calcium hydroxide is used, the gypsum component is produced by neutralization, the gypsum needs to be removed by solid-liquid separation. Examples of the method of solid-liquid separation include, but are not limited to, centrifugation and membrane separation, and the gypsum may also be removed by carrying out plural types of separation steps.

The enzyme to be used may be the same as the one used in the procedure B. The conditions for the enzyme treatment may also be the same as those in the procedure B.

In cases where, after the alkaline treatment, the cellulose-containing biomass is hydrolyzed using an enzyme, the lignin component around the hemicellulose and cellulose components is removed by mixing the cellulose-containing biomass with an aqueous solution containing an alkali and heating the resulting mixture, thereby making the hemicellulose and cellulose components reactive, followed by carrying out enzymatic hydrolysis of hemicellulose having a low crystallinity and cellulose having a high crystallinity which have not been decomposed by the hydrothermal process during the alkaline treatment. More particularly, in the alkaline treatment, hydrolysis of a part of the hemicellulose component contained in the cellulose-containing biomass and partial decomposition of lignin mainly occur, and the resulting hydrolysate is separated into an alkaline solution and the solid contents containing cellulose. The solid contents containing cellulose is then hydrolyzed by preparing the pH and adding an enzyme thereto. In cases where the concentration in the alkaline solution is low, the hydrolysis may be carried out by just adding the enzyme after neutralization, without separation of the solid contents. From the hydrolysis reaction product of the solid contents containing cellulose, monosaccharide components containing glucose and xylose as major components can be obtained. Since the separated/recovered alkaline solution contains, as a major component, xylose, which is a pentose, in addition to lignin, an aqueous sugar solution can be isolated by neutralization of the alkaline solution. The aqueous sugar solution obtained by the neutralization may be mixed with the solid contents, followed by adding an enzyme to the resulting mixture to carry out hydrolysis.

The conditions for the ammonia treatment in the procedure F are based on JP 2008-161125 A and JP 2008-535664 A. For example, the concentration of ammonia to be added to the cellulose-containing biomass is within the range of 0.1 to 15% by weight with respect to the cellulose-containing biomass, and the treatment is carried out at 4 to 200° C., preferably 90 to 150° C. The ammonia to be added may be in the state of either liquid or gas. Further, the form of the ammonia to be added may be either pure ammonia or aqueous ammonia. The number of times of the treatment is not restricted, and 1 or more times of the treatment may be carried out. In particular, in cases where the treatment is carried out 2 or more times, the conditions for the first treatment may be different from those for the second and later treatments.

The treated product obtained by the ammonia treatment needs to be subjected to neutralization of ammonia or removal of ammonia to further carry out hydrolysis reaction using an enzyme. The neutralization may be carried out either for ammonia prepared by removal of the solid contents from the hydrolysate by solid-liquid separation, or in the state in which the solid contents are contained. The acid reagent to be used for the neutralization is not restricted. Examples of the acid reagent include hydrochloric acid, nitric acid and sulfuric acid, and the acid reagent is preferably sulfuric acid in view of avoiding corrosiveness to process piping and avoiding inhibition of fermentation. The ammonia can be removed by maintaining the ammonia-treated product under reduced pressure, to evaporate the ammonia into a gas. The removed ammonia may be recovered and reused.

It is known that, in hydrolysis using an enzyme after ammonia treatment, the crystal structure of cellulose changes by the ammonia treatment and the resulting crystal structure allows the enzyme reaction to occur easily. Therefore, by allowing the enzyme to act on the solid contents after such ammonia treatment, hydrolysis can be carried out efficiently. The enzyme used may be the same as the one used in the procedure B. The conditions for the enzyme treatment may also be the same as those in the procedure B.

In cases where aqueous ammonia is used, the water component, other than ammonia, may give an effect similar to the procedure C (hydrothermal treatment), and hydrolysis of hemicellulose and decomposition of lignin may occur. In cases where treatment with aqueous ammonia is carried out followed by hydrolysis of a cellulose-containing biomass using an enzyme, the lignin component around the hemicellulose and cellulose components is removed by mixing the cellulose-containing biomass with an aqueous solution containing ammonia and heating the resulting mixture, thereby making the hemicellulose and cellulose components reactive, followed by carrying out enzymatic hydrolysis of hemicellulose having a low crystallinity and cellulose having a high crystallinity which have not been decomposed by the hydrothermal process during the ammonia treatment. More particularly, in the treatment by aqueous ammonia, hydrolysis of a part of the hemicellulose component contained in the cellulose-containing biomass and partial decomposition of lignin mainly occur, and the resulting hydrolysate is separated into aqueous ammonia and the solid contents containing cellulose. The solid contents containing cellulose is then hydrolyzed by preparing the pH and adding an enzyme thereto. In cases where the concentration of ammonia is as high as about 100%, a large portion of the ammonia may be removed by degassing, followed by neutralization and addition of an enzyme without separation of the solid contents, to carry out hydrolysis. From the hydrolysis reaction product of the solid contents containing cellulose, monosaccharide components containing glucose and xylose as major components can be obtained. Since the separated/recovered aqueous ammonia contains, as a major component, xylose, which is a pentose, in addition to lignin, an aqueous sugar solution can be isolated by neutralizing the alkaline solution. Further, the aqueous sugar solution obtained by the neutralization may be mixed with the solid contents, followed by addition of an enzyme thereto, to carryout hydrolysis.

The aqueous sugar solution obtained in the Step (1) can be obtained by centrifugation or membrane separation to remove the solid contents, as mentioned above. In such cases, depending on the separation conditions, especially on the separation membrane used, removal of the solid contents may be insufficient, and fine particles may be contained in the solution. Examples of the constituting components of such fine particles include, but are not limited to, lignin, tannin, silica, calcium and undecomposed cellulose. Further, the particle sizes of the fine particles are not restricted. Further, water-soluble macromolecular components may also be contained in addition to the fine particles. Examples of the water-soluble macromolecular components contained in the aqueous sugar solution include oligosaccharides, polysaccharides and tannin, and, in the case of an aqueous sugar solution prepared by using an enzyme, a large amount of the enzyme is contained.

Existence of fine particles or water-soluble macromolecules contained in the aqueous sugar solution may cause fouling during the later-mentioned continuous operation of a nanofiltration membrane and/or reverse osmosis membrane, although the operation is possible. Therefore, the frequency of replacement of the nanofiltration membrane and/or reverse osmosis membrane may increase. In such cases, it is preferred to remove, in the after treatment of the Step (1), fine particles by allowing the aqueous sugar solution to pass through a microfiltration membrane and/or ultrafiltration membrane which can securely remove such fine particles and water-soluble macromolecules. Examples of the filtration include, but are not limited to, pressure filtration, vacuum filtration and centrifugal filtration. Further, the filtering operation is roughly classified into constant pressure filtration, constant flow filtration and non-constant pressure/non-constant flow filtration, but examples of the filtering operation is not limited thereto. The filtration operation may also be a multistep filtration wherein a microfiltration membrane or an ultrafiltration membrane is used 2 or more times for efficient removal of the solid contents. In this case, the material and the properties of the membrane to be used are not restricted.

The microfiltration membrane is a membrane having an average pore size of 0.01 μm to 5 mm, which is called microfiltration, MF membrane or the like for short. The ultrafiltration membrane is a membrane having a molecular weight cutoff of 1,000 to 200,000, which membrane is called ultrafiltration, UF membrane or the like for short. In the ultrafiltration membrane, the pore size is too small to measure the sizes of the pores on the membrane surface under the electron microscope or the like, so that a value called the molecular weight cutoff is used as an index of the size of the pore instead of the average pore size. As described "The curve obtained by plotting the molecular weights of solutes along the abscissa and the blocking rates along the ordinate is called the molecular weight cutoff curve. The molecular weight with which the blocking rate reaches 90% is called the molecular weight cutoff." in p. 92 of The Membrane Society of Japan ed., Membrane Experiment Series, Vol. III, Artificial Membrane, editorial committee members: Shoji Kimura, Shin-ichi Nakao, Haruhiko Ohya and Tsutomu Nakagawa (1993, published by Kyoritsu Shuppan Co., Ltd.), the molecular weight cutoff is well-known to those skilled in the art as an index representing the membrane performance of an ultrafiltration membrane.

The material of the microfiltration membrane or ultrafiltration membrane is not restricted as long as removal of fine particles can be attained therewith, and examples thereof include organic materials such as cellulose, cellulose ester, polysulfone, polyether sulfone, chlorinated polyethylene, polypropylene, polyolefin, polyvinyl alcohol, polymethyl methacrylate, polyvinylidene fluoride and polytetrafluoroethylene; metals such as stainless steel; and inorganic materials such as ceramics. The material of the microfiltration membrane or ultrafiltration membrane may be appropriately selected based on the properties of the hydrolysate and/or the running cost, and the material is preferably an organic material, more preferably chlorinated polyethylene, polypropylene, polyvinylidene fluoride, polysulfone or polyether sulfone.

Further, by filtering the aqueous sugar solution obtained in the Step (1) especially through an ultrafiltration membrane, the enzyme which has been used for saccharification can be recovered from the feed side. The process of recovery of the enzyme will now be described. The enzyme used in the hydrolysis has a molecular weight within the range of 10,000 to 100,000, and, by allowing the sugar liquid obtained in the Step (1) to pass through an ultrafiltration membrane having a molecular weight cutoff with which the enzyme can be blocked, the enzyme can be recovered from the fraction in the feed side. Preferably, by using an ultrafiltration membrane having a molecular weight cutoff within the range of 10,000 to 30,000, the enzyme to be used for the hydrolysis can be efficiently recovered. The form of the ultrafiltration membrane used is not restricted, and may be in the form of either a flat membrane or a hollow fiber. By reusing the recovered cellulase in the hydrolysis in the Step (1), the amount of the enzyme to be used may be reduced. When such filtration of an aqueous sugar solution is carried out using an ultrafiltration membrane, the aqueous sugar solution is preferably preliminarily processed by being allowed to pass through a microfiltration membrane, to remove fine particles.

Examples of the step of processing with a microfiltration membrane and/or ultrafiltration membrane after the Step (1) include the procedure α: a method wherein the liquid is filtered through a microfiltration membrane; the procedure β: a method wherein the liquid is centrifuged and then filtered through a microfiltration membrane; the procedure γ: a method wherein the liquid is centrifuged and then filtered through a microfiltration membrane, followed by being filtered through an ultrafiltration membrane; the procedure δ: solid-liquid separation is carried out using a filter press, and the filtrate is then filtered through an ultrafiltration membrane; and the procedure ε: solid-liquid separation is carried out using a filter press, and microfiltration is then carried out, followed by further filtering the filtrate through an ultrafiltration membrane.

In the procedure a, the sugar liquid obtained in the Step (1) is subjected to solid-liquid separation using only a microfiltration membrane in cases where the amounts of substances which are especially prone to block the surface of the microfiltration membrane, such as the solid components represented by undecomposed cellulose and the gel components derived from macromolecules, are small. In this case, it is possible to remove undecomposed cellulose and inorganic components such as silica having particle diameters of not less than several ten nanometers attached to the biomass. If such solid contents are not removed, when the liquid is allowed to pass through the surface of the nanofiltration membrane and/or reverse osmosis membrane in the Step (2), the membrane surface may be damaged and the membrane may be destroyed, or the solid contents may accumulate on the surface in a short time, leading to decrease in the flux.

Further, in cases where the amounts of solid contents such as undecomposed cellulose are large and the total amount of the liquid cannot be filtered with only a microfiltration membrane because of large decrease in the flux with time, centrifugation is preliminarily carried out and the microfiltration membrane treatment is then carried out by the procedure β, thereby allowing removal of undecomposed cellulose and inorganic components such as silica having particle diameters of not less than several ten nanometers attached to the biomass. In the procedure β, also in cases where the amounts of the solid components and the gel components are small, components having relatively large masses can be preliminarily removed by the centrifugation, so that maintenance of the microfiltration membrane is less necessary, giving the effect of reducing the process cost.

Further, by the procedure γ in which, in addition to the procedure β, treatment with an ultrafiltration membrane is carried out in the subsequent stage, inorganic particle components having sizes of not more than several ten nanometers, which cannot be removed with the microfiltration membrane; water-soluble macromolecular components derived from lignin (tannin); sugars which were hydrolyzed but are still in the middle of the process of decomposition into monosaccharides, which sugars are in the levels of oligosaccharides or polysaccharides; and the enzyme used for the hydrolysis of the sugar; can be removed. In the later-mentioned Step (2), the inorganic particle components may damage and destroy the membrane, or accumulate on the membrane, leading to decrease in the flux. Further, ultrafine particles/clusters having diameters of not more than several nanometers, which usually aggregate and exist as particles/clusters having diameters of several ten nanometers, may penetrate into the inside of the membrane and block the membrane. Similarly, tannin, oligosaccharides, polysaccharides and enzymes may be factors that gel and accumulate on the membrane or block the membrane inside the membrane. Therefore, by additionally carrying out the treatment with an ultrafiltration membrane, membrane fouling in the Step (2) is suppressed, and the maintenance cost for the membrane can be largely reduced. Further, in the case of a step in which an enzyme is used when hydrolysis is carried out, the enzyme can be recovered by using the ultrafiltration membrane, and the enzyme blocked by the ultrafiltration membrane can be reused by being returned to the hydrolysis step in the Step (1), which is advantageous.

Further, in cases where the procedure δ, wherein usage of a filter press, centrifugal filtration, high-speed centrifugation and the like may be carried out to further increase the clarity of the liquid upon the solid-liquid separation, is selected, the microfiltration step may be skipped from the procedure γ and the ultrafiltration membrane step may be directly carried out.

Further, in cases where the clarity of the liquid is low, that is, in cases where the turbidity of the liquid is high, membrane fouling occurs more extensively in the ultrafiltration membrane step, which may lead to increase in the maintenance cost. Therefore, by selecting, depending on the running cost for the ultrafiltration membrane, the procedure ε, which is a high-clarity solid-liquid separation method by carrying out microfiltration membrane treatment before ultrafiltration membrane treatment to prevent fouling of the ultrafiltration membrane, the total running cost for the microfiltration membrane and the ultrafiltration membrane may become lower than in the procedure δ, wherein only an ultrafiltration membrane is used.

The Step (2) of the method for producing the sugar liquid, which is a step of allowing an aqueous sugar solution to pass through a nanofiltration membrane and/or reverse osmosis membrane, recovering a purified sugar liquid from the feed side and removing fermentation-inhibiting substances from the permeate side, will now be described.

The term "fermentation inhibition" means a phenomenon wherein the amount of production, the amount of accumulation or the production rate decreases in cases where a chemical product is produced using, as a fermentation feedstock, a sugar liquid prepared by using a cellulose-containing biomass containing fermentation-inhibiting substances as a raw material, compared to cases where a reagent grade monosaccharide is used as a fermentation feedstock. The extent of such fermentation inhibition is not restricted since the extent to which the microorganism is inhibited varies depending on the types of the fermentation-inhibiting substances existing in the saccharified liquid and the amounts thereof, and the extent of inhibition also varies depending on the species of the microorganism used and the type of the chemical product produced by the microorganism.

Any of the aqueous sugar solutions obtained by the procedures for hydrolysis of the cellulose-containing biomass contains fermentation-inhibiting substances although the amounts or the components thereof vary depending on the procedure or the type of the cellulose-containing biomass as a raw material. Such fermentation-inhibiting substances can be removed by subjecting the aqueous sugar solution to the procedure of the Step (2). The fermentation-inhibiting substances are compounds which are produced by hydrolysis of a cellulose-containing biomass and have inhibitory actions as mentioned above during the step of fermentation using a sugar liquid obtained by our production method. The fermentation-inhibiting substances are produced especially during the step of acid treatment of the cellulose-containing biomass, and roughly classified into organic acids, furan compounds and phenolic compounds.

Examples of the organic acids include acetic acid, formic acid and levulinic acid. Examples of the furan compounds include furfural and hydroxymethylfurfural (MHF). Such organic acids and furan compounds are products produced by decomposition of glucose or xylose, which are monosaccharides.

Particular examples of the phenolic compounds include vanillin, acetovanillin, vanillic acid, syringic acid, gallic acid, coniferyl aldehyde, dihydroconiferyl alcohol, hydroquinone, catechol, acetoguaicone, homovanillic acid, 4-hydroxybenzoic acid, and 4-hydroxy-3-methoxy-phenyl derivatives (Hibbert's ketones). These compounds are derived from lignin or lignin precursors.

Further, in cases where a waste building material, plywood or the like is used as the cellulose-containing biomass, components such as adhesives and paints used in the lumbering process may be contained as fermentation-inhibiting substances. Examples of the adhesives include urea resins, melamine resins, phenol resins, and urea/melamine copolymers. Examples of fermentation-inhibiting substances derived from such adhesives include acetic acid, formic acid and formaldehyde.

The aqueous sugar solution obtained in the Step (1) contains at least one of the substances as a fermentation-inhibiting substance(s), and the aqueous sugar solution actually contains a plurality of the substances. These fermentation-inhibiting substances can be detected and quantified by a common analytical method such as thin layer chromatography, gas chromatography or high performance liquid chromatography.

The nanofiltration membrane is also called a nanofilter (nanofiltration membrane, NF membrane), and generally defined as "a membrane that allows permeation of monovalent ions, but blocks divalent ions." The membrane is considered to have fine voids having sizes of about several nanometers, and mainly used to block fine particles, molecules, ions and salts in water.

The reverse osmosis membrane is also called an RO membrane, and generally defined as "a membrane having a desalination function that can also remove monovalent ions." The membrane is considered to have ultrafine voids having sizes ranging from about several angstroms to several nanometers, and mainly used for removal of ionic components, such as seawater desalination and production of ultrapure water.

The term "filtered through a nanofiltration membrane and/or reverse osmosis membrane" means that a sugar liquid obtained by hydrolysis of a cellulose-containing biomass is filtered through a nanofiltration membrane and/or reverse osmosis membrane to block or separate a sugar liquid containing dissolved sugars, especially dissolved monosaccharides such as glucose and xylose, in the feed side, while allowing fermentation-inhibiting substances to permeate as a permeate or filtrate.

The performance(s) of the nanofiltration membrane and/or reverse osmosis membrane can be evaluated by calculating the permeation rate (%) of a subject compound (a fermentation-inhibiting substance, monosaccharide or the like) contained in the aqueous sugar solution. The method for calculating the permeation rate (%) is as shown in Equation 1:

Permeation rate(%)=(concentration of subject compound in permeate side/concentration of subject compound in non-permeated liquid)×100 (Equation 1).

The method for measuring the concentration of the subject compound in Equation 1 is not restricted as long as the concentration can be measured with high accuracy and reproducibility, and preferred examples of the method include high performance liquid chromatography and gas chromatography. In cases where the subject compound is a monosaccharide, its permeation rate through the nanofiltration membrane and/or reverse osmosis membrane is preferably low, while in cases where the subject compound is a fermentation-inhibiting substance, its permeation rate is preferably high.

In terms of the permeation performance of the nanofiltration membrane, a nanofiltration membrane in which the permeation flow rate of sodium chloride (500 mg/L) per unit membrane area ($m^3/m^2$/day) at a filtration pressure of 0.3 MPa is 0.5 to 0.8 is preferably used. The permeation flow rate per unit membrane area (membrane permeation flux or flux) can be calculated according to Equation 2, by measuring the amount of the liquid permeated, collection time of the permeated liquid, and the membrane area:

Membrane permeation flux($m^3/m^2$/day)=amount of liquid permeated/membrane area/liquid collection time (Equation 2).

The pH of the aqueous sugar solution to be applied to the nanofiltration membrane and/or reverse osmosis membrane is not restricted, and preferably 1 to 5. In cases where the pH is less than 1, the membrane is degraded when it is used for long time, leading to drastic decrease in membrane performances such as the flux and the permeation rate, while in cases where the pH is more than 5, the removal rates of organic acids such as acetic acid, formic acid and levulinic acid may drastically decrease. Since the membrane surface(s) of the nanofiltration membrane and/or reverse osmosis membrane is/are charged, substances ionized in the solution are more prone to be removed or blocked than non-ionized substances, so that, in cases where the contents of organic acids contained in the aqueous sugar solution are high, or in cases where a high removal effect is required, the removal efficiency can be drastically enhanced by adjusting the pH of the aqueous sugar solution to within the above-described range. Another effect of filtering the aqueous sugar solution, whose pH was adjusted to 1 to 5, through the nanofiltration membrane and/or reverse osmosis membrane is the inhibitory effect on fouling of the membrane. In general, the initial flux value decreases as the pH decreases, but, especially in the case of an aqueous sugar solution derived from a cellulose-containing biomass, the stability of the membrane can be maintained longer at a pH of 1 to 5.

Further, especially in the case of a reverse osmosis membrane, the pH of the aqueous sugar solution is preferably adjusted to 1 to 3. Similarly to a nanofiltration membrane, in cases where the pH is less than 1, a reverse osmosis membrane is degraded when it is used for long time, leading to drastic decrease in membrane performances such as the flux and the permeation rate. On the other hand, in cases where the pH is more than 3, the removal rates of organic acids may be insufficient. This may be due to the fact that, because of the smaller pore sizes of a reverse osmosis membrane than those of a nanofiltration membrane, or the like, the ion radius, which is the effective radius of an organic acid, is too large to maintain the removal performance equivalent to that of a nanofiltration membrane without further suppression of the charge derived from the ionicity of the eluted components.

Use of a low-pressure/ultralow-pressure type reverse osmosis membrane with which the operation pressure can be reduced, among reverse osmosis membranes, allows achievement of an organic acid removal rate equivalent to that of an RO membrane which is not a low-pressure/ultralow-pressure type membrane, even in cases where the adjusted pH of the raw liquid is more than 3. Therefore, the effects of reducing the amount of the acid used for the adjustment of the pH and reducing the amount of the alkali used for the adjustment of the pH in the fermentation step in a later process can be obtained, and the removal rates of organic acids are enhanced compared to a reverse osmosis membrane which is not a low-pressure/ultralow-pressure type membrane, so that a low-pressure/ultralow-pressure type reverse osmosis membrane is preferably used. The low-pressure/ultralow-pressure type reverse osmosis membrane means a reverse osmosis membrane in which the permeation flow rate of sodium chloride (500 mg/L) per unit membrane area ($m^3/m^2$/day) at a filtration pressure of 0.75 MPa is not less than 0.4.

The acid or alkali used for adjustment of the pH of the aqueous sugar solution is not restricted. The acid is preferably hydrochloric acid, sulfuric acid, nitric acid or phosphoric acid, more preferably sulfuric acid, nitric acid or phosphoric acid in view of the fact that inhibition during fermentation is less likely to occur, still more preferably sulfuric acid in view of the economic efficiency. The alkali is preferably ammonia, sodium hydroxide or calcium hydroxide, or an aqueous solution containing it in view of the economic efficiency, more preferably ammonia or sodium, which are monovalent ions, in view of membrane fouling, still more preferably ammonia in view of the fact that inhibition during fermentation is less likely to occur.

The stage at which the pH adjustment of the aqueous sugar solution is carried out may be before the nanofiltration membrane and/or reverse osmosis membrane treatment. Further, in cases where an enzyme is used for hydrolysis of the cellulose-containing biomass, the pH may be adjusted to not more than 5 when the hydrolysis reaction is carried out. Further, in cases where the process of reusing the enzyme using an ultrafiltration membrane is employed, the enzyme is likely to be deactivated if the pH decreases to not more than 4, so that the pH of the filtrate after the ultrafiltration membrane treatment is preferably adjusted.

The temperature of the aqueous sugar solution to be subjected to the treatment with a nanofiltration membrane and/or reverse osmosis membrane is not restricted, but the temperature may be set appropriately for the purpose of enhancement of the fermentation-inhibiting substance-removing capacity during the filtration through the membrane used.

More particularly, in cases where the filtration is carried out through a reverse osmosis membrane, the fermentation-inhibiting substance-removing capacity of the reverse osmosis membrane is high if the temperature of the aqueous sugar solution is 40 to 80° C., so that the temperature is preferably set within this range. This is because the removal capacity begins to increase at a temperature of the aqueous sugar solution of 40° C. or higher in cases where the filtration is carried out through a nanofiltration membrane, but a temperature higher than 80° C. may cause degradation of the reverse osmosis membrane, resulting in loss of the membrane properties.

In cases where the filtration is carried out through a nanofiltration membrane, the temperature of the aqueous sugar solution is preferably set within 1 to 15° C. If the temperature of the aqueous sugar solution is less than 1° C. in cases where the filtration is carried out through a nanofiltration membrane, pipes may be frozen inside, causing device errors, while in cases where the temperature is more than 15° C., an effect of reducing the loss does not appear largely. The temperature control is based on the fact that, in cases where the temperature is high, swelling of the membrane occurs, substances having larger molecular weights are removed, and the amount of removal tends to increase, while in cases where the temperature is low, contraction of the membrane occurs and the pore sizes of the membrane decrease, resulting in decrease in the loss of the sugar into the filtrate side.

Since a nanofiltration membrane is generally classified as a membrane having a larger pore size than a reverse osmosis membrane, in cases where a nanofiltration membrane is used in the Step (2), fermentation-inhibiting substances permeate through the membrane and the weights of the substances removed are larger compared to those of a reverse osmosis membrane, but, on the other hand, it is considered that the weights of monosaccharides, which are the products of interest, lost into the permeate side are also large. In particular, in cases where the sugar concentration is high, such a tendency appears strongly. On the other hand, in cases where a reverse osmosis membrane is used in the Step (2), it is considered, because of the small pore sizes, that the weights of inhibitory substances having large molecular weights which can be removed are smaller compared to those in the case of a nanofiltration membrane. Therefore, it is preferred to select an appropriate membrane among nanofiltration membranes and reverse osmosis membranes depending on the weights of the fermentation-inhibiting substances and the molecular weights of the major fermentation-inhibiting substances in the sugar liquid obtained by the above-described treatments. The number of types of the membrane selected is not necessarily one, and plural types of membranes may be selected among nanofiltration membranes and reverse osmosis membranes, to be used in combination for the filtration.

It was discovered that, in cases where a purified sugar liquid is obtained using a nanofiltration membrane, as the purification of monosaccharides captured in the concentrate side of the nanofiltration membrane proceeds and their concentrations increase, the tendency of losing the monosaccharides into the filtrate side sharply increases. On the other hand, in cases where the purification was carried out using a reverse osmosis membrane, the tendency of losing the monosaccharides was constantly almost zero even when the monosaccharide concentration in the concentrate side increased, but, in view removal of fermentation-inhibiting substances, a nanofiltration membrane showed a better performance than a reverse osmosis membrane. Thus, it was discovered that the loss of monosaccharides into the filtrate side can be suppressed while removing large amounts of fermentation-inhibiting substances, by carrying out the purification process using a nanofiltration membrane, with which larger amounts of fermentation-inhibiting substances can be removed compared to a reverse osmosis membrane, to a concentration at which loss of sugars into the filtrate is large, followed by further continuing the purification process using a reverse osmosis membrane, which shows a somewhat smaller efficiency of removal of fermentation-inhibiting substances than a nanofiltration membrane but can concentrate monosaccharides without loss. Therefore, in cases where a nanofiltration membrane and a reverse osmosis membrane are combined to obtain a purified sugar liquid, the combination is not restricted, but it is preferred to filtrate the aqueous sugar solution obtained in the Step (1) first through a nanofiltration membrane, followed by further filtering the obtained filtrate through a reverse osmosis membrane.

Examples of the material of the nanofiltration membrane which may be used include macromolecular materials such as cellulose acetate polymers, polyamides, polyesters, polyimides and vinyl polymers. The membrane is not restricted to a membrane constituted by only one of the materials, and may be a membrane comprising plural membrane materials. In terms of the structure of the membrane, the membrane may be either an asymmetric membrane, which has a dense layer on at least one side and micropores having pore sizes that gradually increase in the direction from the dense layer toward the inside of the membrane or the other side of the membrane, or a composite membrane, which has a very thin functional layer formed by another material on the dense layer of an asymmetric membrane. Examples of the composite membrane which may be used include the composite membrane described in JP 62-201606 A, which has a nanofilter composed of a polyamide functional layer on a support membrane comprising polysulfone as a membrane material.

Among these, a composite membrane having a functional layer composed of a polyamide is preferred since it has a high pressure resistance, high permeability and high solute-removal performance, which make the membrane highly potential. For maintenance of durability against operation pressure, high permeability and high blocking performance, a membrane having a structure in which a polyamide is used as a functional layer, which layer is retained by a support comprising a porous membrane and a non-woven fabric, is suitable. Further, as a polyamide semipermeable membrane, a composite semipermeable membrane having, on a support, a functional layer of a cross-linked polyamide obtained by polycondensation reaction between a polyfunctional amine and a polyfunctional acid halide is suitable.

In the nanofiltration membrane having a functional layer composed of a polyamide, preferred examples of the carboxylic acid component of the monomers constituting the polyamide include aromatic carboxylic acids such as trimesic acid, benzophenone tetracarboxylic acid, trimellitic acid, pyromellitic acid, isophthalic acid, terephthalic acid, naphthalene dicarboxylic acid, diphenylcarboxylic acid and pyridinecarboxylic acid. In view of solubility to film-forming solvents, trimesic acid, isophthalic acid and terephthalic acid, and mixtures thereof are more preferred.

Preferred examples of the amine component of the monomers constituting the polyamide include primary diamines having an aromatic ring, such as m-phenylenediamine, benzidine, methylene bis dianiline, 4,4'-diaminobiphenylether, dianisidine, 3,3',4,4'-triaminobiphenylether, 3,3',4,4'-tetraminobiphenylether, 3,3'-dioxybenzidine, 1,8-naphthalenediamine, m(p)-monomethylphenylenediamine, 3,3'-monomethylamino-4,4'-diaminobiphenylether, 4,N,N'-(4-aminobenzoyl)-p(m)-phenylenediamine-2,2'-bis(4-aminophenylbenzoimidazole), 2,2'-bis(4-aminophenylbenzooxazole) and 2,2'-bis(4-aminophenylbenzothiazole); and secondary diamines such as piperazine, piperidine and derivatives thereof. Among these, a nanofiltration membrane having a functional layer composed of a cross-linked polyamide comprising piperazine or piperidine as monomers is preferably used since it has heat resistance and chemical resistance in addition to the pressure resistance and the durability. The polyamide more preferably contains as a major component the cross-linked piperazine polyamide or cross-linked piperidine polyamide and further contains a constituting component represented by Formula 1, still more preferably contains a cross-linked piperazine polyamide as a major component and further contains a constituting component represented by Formula 1. Further, preferably, in Formula 1, n=3. Examples of the nanofiltration membrane having a functional layer composed of a polyamide containing a cross-linked piperazine polyamide as a major component and further containing a constituting component represented by Formula 1 include the one described in JP 62-201606 A, and particular examples thereof include UTC60 manufactured by TORAY INDUSTRIES, INC., which is a cross-linked piperazine polyamide nanofiltration membrane having a functional layer composed of a polyamide containing a cross-linked piperazine polyamide as a major component and further containing a constituting component represented by Formula 1, wherein n=3.

A nanofiltration membrane is generally used as a spiral-wound membrane module, and the nanofiltration membrane is also preferably used as a spiral-wound membrane module. Particular preferred examples of the nanofiltration membrane module include GEsepa, which is a cellulose acetate nanofiltration membrane manufactured by GE Osmonics; NF99 and NF99HF, which are nanofiltration membranes having a functional layer composed of a polyamide, manufactured by Alfa-Laval; NF-45, NF-90, NF-200, NF-270 and NF-400, which are nanofiltration membranes having a functional layer composed of a cross-linked piperazine polyamide, manufactured by Filmtec Corporation; and SU-210, SU-220, SU-600 and SU-610, which are nanofiltration membrane modules manufactured by TORAY INDUSTRIES, INC., having UTC60 manufactured by the same manufacturer, which has a functional layer composed of a polyamide containing a cross-linked piperazine polyamide as a major component and further containing a constituting component represented by Formula 1. The nanofiltration membrane module is more preferably NF99 or NF99HF, which are nanofiltration membranes having a functional layer composed of a polyamide, manufactured by Alfa-Laval; NF-45, NF-90, NF-200 or NF-400, which are nanofiltration membranes having a functional layer composed of a cross-linked piperazine polyamide, manufactured by Filmtec Corporation; or SU-210, SU-220, SU-600 or SU-610, which are nanofiltration membrane modules manufactured by TORAY INDUSTRIES, INC., having UTC60 manufactured by the same manufacturer, which has a functional layer composed of a polyamide containing a cross-linked piperazine polyamide as a major component and further containing a constituting component represented by Formula 1. The nanofiltration membrane module is still more preferably SU-210, SU-220, SU-600 or SU-610, which are nanofiltration membrane modules manufactured by TORAY INDUSTRIES, INC., having UTC60 manufactured by the same manufacturer, which has a functional layer composed of a polyamide containing a cross-linked piperazine polyamide as a major component and further containing a constituting component represented by Formula 1.

The filtration through a nanofiltration membrane in the Step (2) may be carried out under pressure, and the filtration pressure is preferably within the range of 0.1 to 8 MPa. In cases where the filtration pressure is less than 0.1 MPa, the membrane permeation rate may decrease, while in cases where the filtration pressure is more than 8 MPa, the membrane may be damaged. In cases where the filtration pressure is within the range of 0.5 to 7 MPa, the membrane permeation flux is high, so that the sugar solution can be efficiently allowed to permeate and the possibility of damaging the membrane is small, which is more preferred. The range is especially preferably 1 to 6 MPa.

In terms of the material of the reverse osmosis membrane, examples of the membrane include a composite membrane having a functional layer composed of a cellulose acetate polymer (hereinafter also referred to as a cellulose acetate reverse osmosis membrane) and a composite membrane having a functional layer composed of a polyamide (hereinafter also referred to as a polyamide reverse osmosis membrane). Examples of the cellulose acetate polymer include polymers prepared with organic acid esters of cellulose such as cellulose acetate, cellulose diacetate, cellulose triacetate, cellulose propionate and cellulose butyrate, which may be used solely, as a mixture, or as a mixed ester. Examples of the polyamide include linear polymers and cross-linked polymers constituted by aliphatic and/or aromatic diamine monomers.

Particular examples of the reverse osmosis membrane include polyamide reverse osmosis membrane modules manufactured by TORAY INDUSTRIES, INC., such as ultralow-pressure type modules SUL-G10 and SUL-G20, low-pressure type modules SU-710, SU-720, SU-720F, SU-710L, SU-720L, SU-720LF, SU-720R, SU-710P and SU-720P, as well as high-pressure type modules SU-810, SU-820, SU-820L and SU-820FA containing UTC80 as the reverse osmosis membrane; cellulose acetate reverse osmosis membranes manufactured by the same manufacturer SC-L100R, SC-L200R, SC-1100, SC-1200, SC-2100, SC-2200, SC-3100, SC-3200, SC-8100 and SC-8200; NTR-759HR, NTR-729HF, NTR-70SWC, ES10-D, ES20-D, ES20-U, ES15-D, ES15-U and LF10-D manufactured by Nitto Denko Corporation; RO98pHt, RO99, HR98PP and CE4040C-30D manufactured by Alfa-Laval; GE Sepa manufactured by GE; BW30-4040, TW30-4040, XLE-4040, LP-4040, LE-4040, SW30-4040 and SW30HRLE-4040 manufactured by FilmTec Corporation; TFC-HR and TFC-ULP manufactured by KOCH; and ACM-1, ACM-2 and ACM-4 manufactured by TRISEP.

A reverse osmosis membrane having a polyamide material is preferably used. This is because, when a cellulose acetate membrane is used for a long time, enzymes used in the previous step, especially a part of the cellulase component, may permeate into the membrane to decompose cellulose as a membrane material.

Examples of the form of the membrane which may be used as appropriate include the flat membrane, spiral-wound membrane and hollow fiber membrane.

The filtration through a reverse osmosis membrane in the Step (2) may be carried out under pressure, and the filtration pressure is preferably within the range of 0.1 to 8 MPa. In cases where the filtration pressure is less than 0.1 MPa, the membrane permeation rate may decrease, while in cases where the filtration pressure is more than 8 MPa, the membrane may be damaged. In cases where the filtration pressure is within the range of 0.5 to 7 MPa, the membrane permeation flux is high, so that the sugar solution can be efficiently allowed to permeate and the possibility of damaging the membrane is small, which is more preferred. The range is especially preferably 1 to 6 MPa.

In the Step (2), the fermentation-inhibiting substances are removed from the aqueous sugar solution by being allowed to permeate through the nanofiltration membrane and/or reverse osmosis membrane. Among the fermentation-inhibiting substances, HMF, furfural, acetic acid, formic acid, levulinic acid, vanillin, acetovanillin and syringic acid can be preferably allowed to permeate/removed. On the other hand, sugars contained in the aqueous sugar solution are blocked or separated in the feed side of the nanofiltration membrane and/or reverse osmosis membrane. The sugars contain monosaccharides such as glucose and xylose as major components, and also contain sugar components which have not been completely decomposed into monosaccharides during the hydrolysis process in the Step (1), such as disaccharides and oligosaccharides.

In the Step (2), when compared with the aqueous sugar solution before being passed through the nanofiltration membrane and/or reverse osmosis membrane, the purified sugar liquid obtained from the feed side of the nanofiltration membrane and/or reverse osmosis membrane has reduced contents of especially fermentation-inhibiting substances relative to their initial contents. The sugar components contained in the purified sugar liquid are sugars derived from the cellulose-containing biomass, and, essentially, these are not largely different from the sugar components obtained by the hydrolysis in the Step (1). That is, the monosaccharides contained in the purified sugar liquid comprise glucose and/or xylose as a major component(s). The ratio between glucose and xylose varies depending on the step of hydrolysis in the Step (1), and is not restricted. That is, in cases where the hydrolysis is carried out mainly for hemicellulose, xylose is the major monosaccharide component, while in cases where hemicellulose is decomposed and only the cellulose component is then separated and hydrolyzed, glucose is the major monosaccharide component. Further, in cases where the decomposition of hemicellulose, the decomposition of cellulose and the separation are not carried out, glucose and xylose are contained as the major monosaccharide components.

The purified sugar liquid obtained in the Step (2) may once be concentrated using a concentrator such as an evaporator, or the purified sugar liquid may be further filtered through a nanofiltration membrane and/or reverse osmosis membrane to increase the concentration. In view of reducing energy for the concentration, the step of further increasing the concentration by filtering the purified sugar liquid through a nanofiltration membrane and/or reverse osmosis membrane is preferably employed. The membrane used in this concentration step is a membrane filter that removes ions and low-molecular-weight molecules using a pressure difference larger than the osmotic pressure of the liquid to be treated as the driving force, and examples thereof which can be used include cellulose membranes such as those made of cellulose acetate and membranes produced by polycondensing a polyfunctional amine compound and a polyfunctional acid halide to provide a separation functional layer made of a polyamide on a microporous support membrane. To suppress dirt, that is, fouling, on the surface(s) of the nanofiltration membrane and/or reverse osmosis membrane, a low-fouling reverse osmosis membrane, which is mainly for sewage treatment, can also be preferably employed, which low-fouling reverse osmosis membrane is prepared by covering the surface of a separation functional layer made of a polyamide with an aqueous solution of a compound having at least one reactive group reactive with an acid halide group, thereby allowing acid halide groups remaining on the surface of the separation functional layer to form covalent bonds with the reactive groups. As the nanofiltration membrane and/or reverse osmosis membrane to be used, one having higher blocking rates of monosaccharides such as glucose and xylose than the nanofiltration membrane and/or reverse osmosis membrane used in the Step (2) may be more preferably used.

Particular examples of the nanofiltration membrane or reverse osmosis membrane used for the concentration are the same as the particular examples of the nanofiltration membrane or reverse osmosis membrane described above.

The water discharged as the filtrate in the Step (2) may be reused in a step of producing a sugar such as hydrolysis or sugar purification, or in a later step of producing a chemical product such as fermentation or chemical product purification. Further, the filtrate may be filtered through a nanofiltration membrane and/or reverse osmosis membrane once again before the reuse. More preferably, the pH is adjusted to 1 to 5 and the liquid is purified using a nanofiltration membrane and/or reverse osmosis membrane, followed by filtering the filtrate through a nanofiltration membrane and/or reverse osmosis membrane and carrying out the reuse. Still more preferably, the pH is adjusted to 1 to 5 and the liquid is purified through a nanofiltration membrane and/or reverse osmosis membrane, followed by increasing the pH again, selectively removing especially organic acids using a nanofiltration membrane and/or reverse osmosis membrane, and carrying out the reuse.

The method for producing a chemical product using, as a fermentation feedstock, a purified sugar liquid obtained by the method for producing a sugar liquid will now be described.

By using a purified sugar liquid as a fermentation feedstock, a chemical product can be produced. The obtained purified sugar liquid contains, as major components, glucose and/or xylose, which are carbon sources for growth of microorganisms or cultured cells. On the other hand, the contents of fermentation-inhibiting substances such as furan compounds, organic acids and aromatic compounds are very small. Therefore, the purified sugar liquid can be effectively used as a fermentation feedstock, especially as a carbon source.

Examples of the microorganisms or cultured cells used in the method for producing a chemical product include yeasts such as baker's yeast, which are commonly used in the fermentation industry; bacteria such as *E. coli* and coryneform bacteria; filamentous fungi; actinomycetes; animal cells; and insect cells. The microorganisms or cultured cells used may be those isolated from a natural environment, or may be those whose properties were partially modified by mutation or gene recombination. In particular, since a sugar liquid derived from a cellulose-containing biomass contains pentoses such as xylose, microorganisms whose metabolic pathways for pentoses were enhanced may be preferably used.

As the medium used in the method for producing a chemical product, a liquid medium containing, in addition to the purified sugar liquid, nitrogen sources, inorganic salts, and, as required, organic micronutrients such as amino acids and vitamins is preferably used. The purified sugar liquid contains as carbon sources monosaccharides which can be used by microorganisms, such as glucose and xylose, but, in some cases, sugars such as glucose, sucrose, fructose, galactose and lactose; saccharified starch liquids containing these sugars; sweet potato molasses; sugar beet molasses; high test molasses; organic acids such as acetic acid; alcohols such as ethanol; glycerin; and the like may be further added as carbon sources, to use the purified sugar liquid as a fermentation feedstock. Examples of the nitrogen sources used include ammonia gas, aqueous ammonia, ammonium salts, urea and nitric acid salts; and other organic nitrogen sources used supplementarily such as oilcakes, soybean-hydrolyzed liquids, casein digests, other amino acids, vitamins, corn steep liquors, yeasts or yeast extracts, meat extracts, peptides such as peptones, and cells of various fermentation microorganisms and hydrolysates thereof. Examples of the inorganic salts which may be added as appropriate include phosphoric acid salts, magnesium salts, calcium salts, iron salts and manganese salts.

In cases where the microorganism requires particular nutrients for its growth, the nutrients may be added as preparations or natural products containing these. An antiforming agent may also be added as required.

Culturing of the microorganism is usually carried out at a pH within the range of 4 to 8, at a temperature within the range of 20 to 40° C. The pH of the culture medium is adjusted in advance with an inorganic or organic acid, alkaline substance, urea, calcium carbonate, ammonia gas or the like to a predetermined pH within the range of, usually, 4 to 8. In cases where the feed rate of oxygen needs to be increased, a method can be employed in which the oxygen concentration is maintained at not less than 21% by adding oxygen into the air; the culturing is carried out under pressure; the stirring rate is increased; the ventilation volume is increased; or the like.

As the method for producing a chemical product using, as a fermentation feedstock, a purified sugar liquid obtained by the method for producing a sugar liquid, a fermentation culture method known to those in the art may be employed, but, in view of productivity, the continuous culture method disclosed in WO2007/097260 is preferably employed.

The chemical product produced by the method for producing a chemical product is not restricted as long as it is a substance produced in the culture medium by the above microorganism or cells. Particular examples of the chemical product produced include alcohols, organic acids, amino acids and nucleic acids, which are substances mass-produced in the fermentation industry. Examples the substances include alcohols such as ethanol, 1,3-propanediol, 1,4-propanediol and glycerol; organic acids such as acetic acid, lactic acid, pyruvic acid, succinic acid, malic acid, itaconic acid and citric acid; nucleic acids such as nucleosides including inosine and guanosine, and nucleotides including inosinic acid and guanylic acid; and diamine compounds such as cadaverine. Further, our methods may also be applied to production of substances such as enzymes, antibiotics and recombinant proteins.

EXAMPLES

The method for producing a sugar liquid will now be described in more detail by way of Examples. However, the method is not restricted to these Examples.

Reference Example 1: Method for Analyzing Monosaccharide Concentration

The concentrations of monosaccharides contained in the obtained aqueous sugar solution were quantified under the HPLC conditions described below, based on comparison with standard samples:
  Column: Luna $NH_2$ (manufactured by Phenomenex, Inc.)
  Mobile phase: ultrapure water:acetonitrile=25:75 (flow rate, 0.6 mL/min.)
  Reaction solution: none
  Detection method: RI (differential refractive index)
  Temperature: 30° C.

Reference Example 2: Method for Analyzing Concentrations of Fermentation-Inhibiting Substances Furan-based fermentation-inhibiting substances (HMF, furfural) and phenol-based fermentation-inhibiting substances (vanillin, acetovanillin, syringic acid, levulinic acid and 4-hydroxybenzoic acid) contained in the sugar liquid were quantified under the HPLC conditions described below, based on comparison with standard samples:
  Column: Synergi HidroRP 4.6 mm×250 mm (manufactured by Phenomenex, Inc.)
  Mobile phase: acetonitrile-0.1% $H_3PO_4$ (flow rate, 1.0 mL/min.)
  Detection method: UV (283 nm)
  Temperature: 40° C.
  Organic acid-based fermentation-inhibiting substances (acetic acid, formic acid) contained in the sugar liquid were quantified under the HPLC conditions described below, based on comparison with standard samples:
  Column: Shim-Pack SPR-H and Shim-Pack SCR101H (manufactured by Shimadzu Corporation) in series
  Mobile phase: 5 mM p-toluenesulfonic acid (flow rate, 0.8 mL/min.)
  Reaction solution: 5 mM p-toluenesulfonic acid, 20 mM Bis-Tris, 0.1 mM EDTA-2Na (flow rate, 0.8 mL/min.)
  Detection method: electric conductivity
  Temperature: 45° C.

Reference Example 3: Step of Hydrolysis of Cellulose-Containing Biomass by Dilute Sulfuric Acid/Enzyme Treatment In terms of the step of hydrolysis of a cellulose-containing biomass in the Step (1), an example of the method of hydrolysis of a cellulose-containing biomass using 0.1 to 15% by weight of dilute sulfuric acid and an enzyme is described.

As a cellulose-containing biomass, rice straw was used. The cellulose-containing biomass was soaked in 1% aqueous sulfuric acid solution, and subjected to treatment using an autoclave (manufactured by Nitto Koatsu Co., Ltd.) at 150° C. for 30 minutes. After the treatment, solid-liquid separation was carried out to separate sulfuric acid-treated cellulose from the aqueous sulfuric acid solution (hereinafter referred to as "dilute-sulfuric-acid treatment liquid"). Subsequently, the sulfuric acid-treated cellulose was mixed with the dilute-sulfuric-acid treatment liquid with stirring such that the concentration of the solid contents is 10% by weight, and the pH was adjusted to about 5 with sodium hydroxide. To this mixture, Trichoderma cellulase (Sigma Aldrich Japan) and Novozyme 188 (Aspergillus niger-derived β-glucosidase preparation, Sigma Aldrich Japan) were added as cellulases, and the resulting mixture was mixed by stirring at 50° C. for 3 days to allow hydrolysis reaction to proceed. Thereafter, centrifugation (3000 G) was carried out to separate/remove undecomposed cellulose and lignin, to obtain an aqueous sugar solution. The turbidity of the aqueous sugar solution was 700 NTU. The compositions of the fermentation-inhibiting substances and the monosaccharides contained in the aqueous sugar solution were as shown in Tables 1 and 2.

TABLE 1

Quantification of Fermentation-inhibiting Substances

|  | Dilute-sulfuric-acid treatment liquid | Aqueous sugar solution |
|---|---|---|
| Formic acid | 0.1 g/L | 0.1 g/L |
| Acetic acid | 2.0 g/L | 2.4 g/L |
| HMF | 100 mg/L | 125 mg/L |
| Furfural | 560 mg/L | 875 mg/L |
| Vanillin | 60 mg/L | 90 mg/L |
| Acetovanillin | 120 mg/L | 146 mg/L |
| Syringic acid | 10 mg/L | 15 mg/L |
| Levulinic acid | 9 mg/L | 10 mg/L |

TABLE 2

Quantification of Monosaccharides

|  | Dilute-sulfuric-acid treatment liquid | Aqueous sugar solution |
|---|---|---|
| Glucose | 3 g/L | 25 g/L |
| Xylose | 15 g/L | 12 g/L |
| Arabinose | 0.8 g/L | 1 g/L |
| Mannose | 0.9 g/L | 1 g/L |

Reference Example 4: Step of Hydrolysis of Cellulose-Containing Biomass by Hydrothermal Treatment/Enzyme Treatment In terms of the step of hydrolysis of a cellulose-containing biomass in the Step (1), an example of the method of hydrolysis of a cellulose-containing biomass using hydrothermal treatment and an enzyme is described.

As a cellulose-containing biomass, rice straw was used. The cellulose-containing biomass was soaked in water, and subjected to treatment using an autoclave (manufactured by Nitto Koatsu Co., Ltd.) at 180° C. for 20 minutes with stirring. The treatment was carried out at a pressure of 10 MPa. After the treatment, solid-liquid separation was carried out by centrifugation (3000 G) to separate the processed biomass component from the solution component (hereinafter referred to as "hydrothermally treated liquid"). The pH of the hydrothermally treated liquid was 4.0, and the turbidity of the hydrothermally treated liquid was 800 NTU.

Thereafter, the water content of the processed biomass component was measured, and RO water was added to the component such that the concentration of the solid contents is 15% by weight in terms of the absolute dry processed biomass, followed by further adding, as cellulases, Trichoderma cellulase (Sigma Aldrich Japan) and Novozyme 188 (Aspergillus niger-derived β-glucosidase preparation, Sigma Aldrich Japan) thereto and mixing the resulting mixture by stirring at 50° C. for 3 days to allow hydrolysis reaction. Thereafter, centrifugation (3000 G) was carried out to separate/remove undecomposed cellulose and lignin, to obtain an aqueous sugar solution. The pH of the aqueous sugar solution was 5.2, and the turbidity of the aqueous sugar solution was 900 NTU. The compositions of the fermentation-inhibiting substances and the monosaccharides contained in the hydrothermally treated liquid and the aqueous sugar solution were as shown in Tables 3 and 4.

TABLE 3

Quantification of fermentation-inhibiting substances

|  | Hydrothermally treated liquid | Aqueous sugar solution |
|---|---|---|
| Formic acid | 1.1 g/L | 0.1 g/L |
| Acetic acid | 2.2 g/L | 0.5 g/L |
| HMF | 139 mg/L | 10 mg/L |
| Furfural | 8 mg/L | 15 mg/L |
| Vanillin | 50 mg/L | 3 mg/L |
| Acetovanillin | 2 mg/L | 13 mg/L |
| Syringic acid | 1 mg/L | 1 mg/L |

TABLE 4

Quantification of Monosaccharides

|  | Hydrothermally treated liquid | Aqueous sugar solution |
|---|---|---|
| Glucose | 2 g/L | 50 g/L |
| Xylose | 15 g/L | 8 g/L |
| Arabinose | 0.5 g/L | 1 g/L |
| Mannose | 0.5 g/L | 0.5 g/L |

Reference Example 5: Step of Hydrolysis of Cellulose-Containing Biomass by Ammonia Treatment/Enzyme Treatment In terms of the step of hydrolysis of a cellulose-containing biomass in the Step (1), an example of the method of hydrolysis of a cellulose-containing biomass using 5.0 to 100% by weight of aqueous ammonia and an enzyme is described. As a cellulose-containing biomass, rice straw was used. The cellulose-containing biomass was fed into a small reactor (manufactured by Taiatsu Techno Corporation, TVS-N2 30 mL), and cooled with liquid nitrogen. Into this reactor, ammonia gas was flown, and the sample was completely soaked in liquid ammonia. The lid of the reactor was closed, and the reactor was left to stand at room temperature for about 15 minutes. Subsequently, the reactor was processed in an oil bath at 150° C. for 1 hour. Thereafter, the reactor was removed from the oil bath, and the ammonia gas was leaked in a fume hood, followed by vacuuming the inside of the reactor to 10 Pa with a vacuum pump, thereby drying the cellulose-containing biomass. This processed cellulose-containing biomass was mixed with pure water by stirring such that the concentration of the solid contents is 15% by weight, and the pH was adjusted to about 5 with sulfuric acid. To this mixture, *Trichoderma* cellulase (Sigma Aldrich Japan) and Novozyme 188 (*Aspergillus niger*-derived β-glucosidase preparation, Sigma Aldrich Japan) were added as cellulases, and the resulting mixture was mixed by stirring at 50° C. for 3 days to allow hydrolysis reaction. Thereafter, centrifugation (3000 G) was carried out to separate/remove undecomposed cellulose and lignin, to obtain an aqueous sugar solution. The turbidity of the aqueous sugar solution was 600 NTU. The compositions of the fermentation-inhibiting substances and the monosaccharides contained in the aqueous sugar solution were as shown in Tables 5 and 6.

TABLE 5

Quantification of fermentation-inhibiting substances

| | Aqueous sugar solution |
|---|---|
| Formic acid | 1.1 g/L |
| Acetic acid | 0.5 g/L |
| HMF | 500 mg/L |
| Furfural | 5 mg/L |
| Vanillin | 20 mg/L |
| Acetovanillin | 18 mg/L |
| Syringic acid | 2 mg/L |

TABLE 6

Quantification of monosaccharides

| | Aqueous sugar solution |
|---|---|
| Glucose | 50 g/L |
| Xylose | 25 g/L |
| Arabinose | 2 g/L |
| Mannose | 1 g/L |

Figure 2:
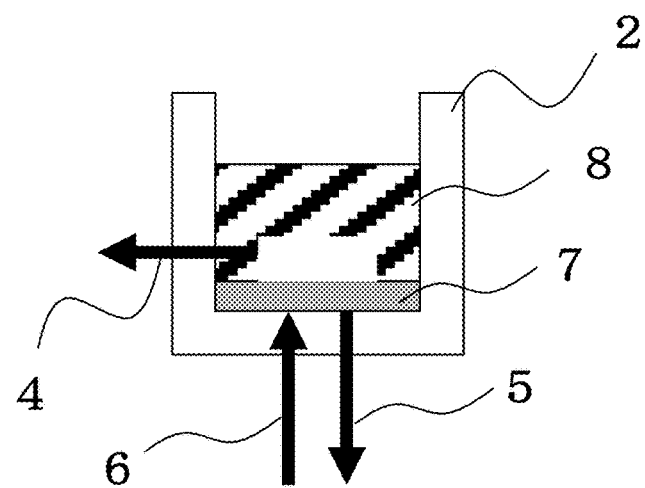
FIG. 2 shows a schematic view of the stainless steel cell which was used in the flat membrane test.

Example 1: Step of Filtering Dilute Sulfuric Acid/Enzyme-Treated Aqueous Sugar Solution through Nanofiltration Membrane or Reverse Osmosis Membrane A step of filtering the aqueous sugar solution obtained in Reference Example 3 through a nanofiltration membrane (NF membrane) or reverse osmosis membrane (RO membrane) and collecting a purified sugar liquid from the feed side, while removing fermentation-inhibiting substances from the permeate side is described by way of an Example. Through a PVDF membrane having a pore size of 0.05 µm, 20 L of the aqueous sugar solution obtained in Reference Example 3 was filtered, and the filtrate was processed through a nanofiltration membrane or reverse osmosis membrane module. Into the raw liquid tank 1 of the membrane filtration apparatus shown in FIG. 1, 20 L of the aqueous sugar solution obtained in Example 2 was fed. Thereafter, 200 L of RO water was added to the raw liquid tank 1. As a nanofiltration membrane, a cross-linked piperazine polyamide nanofiltration membrane UTC60 (manufactured by TORAY INDUSTRIES, INC.) was set, or, as an RO membrane, a cross-linked wholly aromatic polyamide reverse osmosis membrane UTC80 (manufactured by TORAY INDUSTRIES, INC.) was set, which membrane is indicated by the symbol 7 in FIG. 2. The temperature of the raw liquid was adjusted to 25° C. and the pressure by the high-pressure pump 3 was adjusted to 3 MPa, thereby removing the permeate. A total of 200 L of the permeate was removed, and, to the solution remained in the raw liquid tank, whose volume was a little less than 20 L, RO water was added to attain a final volume of 20 L. The resulting dilution was used as a purified sugar liquid.

Fermentation-inhibiting substances (HMF, furfural, vanillin, acetovanillin and syringic acid) contained in the aqueous sugar solution obtained in Reference Example 3 and in the above purified sugar liquids were quantified under the HPLC conditions described in Reference Example 1, based on comparison with standard samples. Further, the concentrations of monosaccharides were quantified under the HPLC conditions described in Reference Example 1, based on comparison with standard samples. The results are summarized in Tables 7 and 8. It was shown by the analysis that, as fermentation-inhibiting substances, acetic acid, formic acid, furfural, HMF, vanillin, acetovanillin, syringic acid and levulinic acid were contained. Further, in terms of monosaccharides contained in the respective sugar liquids, glucose and xylose were the major components. Further, although the amounts were very small, arabinose and mannose were also detected. Further, the purified sugar liquids were confirmed to have largely reduced amounts of fermentation-inhibiting substances compared to the aqueous sugar solution obtained in Reference Example 3. On the other hand, since the concentrations of sugars were not largely decreased in the purified sugar liquids, it could be confirmed that processing of the aqueous sugar solution through the nanofiltration membrane or reverse osmosis membrane allows removal of fermentation-inhibiting substances as the permeate, while allowing recovery of a purified sugar liquid, in which the concentrations of fermentation-inhibiting substances are decreased, from the feed side.

TABLE 7

Quantification of fermentation-inhibiting substances

| | Aqueous sugar solution | NF membrane-purified sugar liquid | RO membrane-purified sugar liquid |
|---|---|---|---|
| Formic acid | 0.1 g/L | 0 g/L | 0 g/L |
| Acetic acid | 2.4 g/L | 0.2 g/L | 1.2 g/L |
| HMF | 125 mg/L | 18 mg/L | 90 mg/L |
| Furfural | 875 mg/L | 88 mg/L | 240 g/L |
| Vanillin | 90 mg/L | 2.7 mg/L | 62 mg/L |
| Acetovanillin | 146 mg/L | 9 mg/L | 103 mg/L |
| Syringic acid | 15 mg/L | 0 mg/L | 10 mg/L |
| Levulinic acid | 10 mg/L | 0 mg/L | 3 mg/L |

TABLE 8

Quantification of monosaccharides

| | Aqueous sugar solution | NF membrane-purified sugar liquid | RO membrane-purified sugar liquid |
|---|---|---|---|
| Glucose | 25 g/L | 24 g/L | 25 g/L |
| Xylose | 12 g/L | 11.2 g/L | 12 g/L |
| Arabinose | 1 g/L | 0.96 g/L | 1 g/L |
| Mannose | 1 g/L | 0.98 g/L | 1 g/L |

Example 2: Step of Filtering Hydrothermally Treated/Enzyme-Treated Aqueous Sugar Solution Through Nanofiltration Membrane or Reverse Osmosis Membrane In terms of the step of filtering the aqueous sugar solution obtained in Reference Example 4 through a nanofiltration membrane or reverse osmosis membrane and collecting a purified sugar liquid from the feed side, while removing fermentation-inhibiting substances from the permeate side, a purified sugar liquid was obtained in the same manner as in Example 1, and the concentrations of fermentation-inhibiting substances and monosaccharides were quantified. The results are summarized in Tables 9 and 10. It was shown by the analysis that, as fermentation-inhibiting substances, acetic acid, formic acid, furfural, HMF, vanillin, acetovanillin and syringic acid were contained. Further, in terms of monosaccharides contained in the respective sugar liquids, glucose and xylose were the major components. Further, although the amounts were very small, arabinose and mannose were also detected.

TABLE 9

Quantification of fermentation-inhibiting substances

|  | Aqueous sugar solution | NF membrane-purified sugar liquid | RO membrane-purified sugar liquid |
| --- | --- | --- | --- |
| Formic acid | 0.1 g/L | 0 g/L | 0 g/L |
| Acetic acid | 0.5 g/L | 0 g/L | 0.2 g/L |
| HMF | 10 mg/L | 1 mg/L | 6 mg/L |
| Furfural | 15 mg/L | 0 mg/L | 3 g/L |
| Vanillin | 3 mg/L | 0 mg/L | 1 mg/L |
| Acetovanillin | 13 mg/L | 1 mg/L | 3 mg/L |
| Syringic acid | 1 mg/L | 0 mg/L | 0 mg/L |

TABLE 10

Quantification of monosaccharides

|  | Aqueous sugar solution | NF membrane-purified sugar liquid | RO membrane-purified sugar liquid |
| --- | --- | --- | --- |
| Glucose | 50 g/L | 49 g/L | 50 g/L |
| Xylose | 8 g/L | 7.2 g/L | 8 g/L |
| Arabinose | 1 g/L | 0.96 g/L | 1 g/L |
| Mannose | 0.5 g/L | 0.48 g/L | 0.5 g/L |

The respective purified sugar liquids were confirmed to have largely reduced amounts of fermentation-inhibiting substances compared to the aqueous sugar solution obtained in Reference Example 4. On the other hand, since the concentrations of sugars were not largely decreased in the purified sugar liquids, it could be confirmed that processing of the aqueous sugar solution through the nanofiltration membrane or reverse osmosis membrane allows removal of fermentation-inhibiting substances as the permeate, while allowing recovery of a purified sugar liquid, in which the concentrations of fermentation-inhibiting substances are decreased, from the feed side.

Example 3: Step of Filtering Ammonia-Treated/Enzyme-Treated Aqueous Sugar Solution Through Nanofiltration Membrane or Reverse Osmosis Membrane In terms of the step of filtering the aqueous sugar solution obtained in Reference Example 5 through a nanofiltration membrane or reverse osmosis membrane and collecting a purified sugar liquid from the feed side, while removing fermentation-inhibiting substances from the permeate side, a purified sugar liquid was obtained in the same manner as in Example 1, and the concentrations of fermentation-inhibiting substances and monosaccharides were quantified. The results are summarized in Tables 11 and 12. It was shown by the analysis that, as fermentation-inhibiting substances, acetic acid, formic acid, furfural, HMF, vanillin, acetovanillin and syringic acid were contained. Further, in terms of monosaccharides contained in the respective sugar liquids, glucose and xylose were the major components. Further, although the amounts were very small, arabinose and mannose were also detected.

TABLE 11

Quantification of fermentation-inhibiting substances

|  | Aqueous sugar solution | NF membrane-purified sugar liquid | RO membrane-purified sugar liquid |
| --- | --- | --- | --- |
| Formic acid | 1.1 g/L | 0 g/L | 0.3 g/L |
| Acetic acid | 0.5 g/L | 0 g/L | 0.2 g/L |
| HMF | 500 mg/L | 10 mg/L | 120 mg/L |
| Furfural | 5 mg/L | 0 mg/L | 1 mg/L |
| Vanillin | 20 mg/L | 0.4 mg/L | 12 mg/L |
| Acetovanillin | 18 mg/L | 1 mg/L | 8 mg/L |
| Syringic acid | 2 mg/L | 0 mg/L | 1 mg/L |

TABLE 12

Quantification of monosaccharides

|  | Aqueous sugar solution | NF membrane-purified sugar liquid | RO membrane-purified sugar liquid |
| --- | --- | --- | --- |
| Glucose | 50 g/L | 49 g/L | 50 g/L |
| Xylose | 25 g/L | 21 g/L | 25 g/L |
| Arabinose | 2 g/L | 1.8 g/L | 2 g/L |
| Mannose | 1 g/L | 0.9 g/L | 1 g/L |

The respective purified sugar liquids were confirmed to have largely reduced amounts of fermentation-inhibiting substances compared to the aqueous sugar solution obtained in Reference Example 5. On the other hand, since the concentrations of sugars were not largely decreased, it could be confirmed that processing of the aqueous sugar solution through the NF membrane or RO membrane allows removal of fermentation-inhibiting substances as the permeate, while allowing recovery of a purified sugar liquid, in which the concentrations of fermentation-inhibiting substances are decreased, from the feed side.

Example 5: Step of Filtering Hydrothermally Treated Liquid Through Nanofiltration Membrane or Reverse Osmosis Membrane In terms of the step of filtering the hydrothermally treated liquid obtained in Reference Example 4 through a nanofiltration membrane or reverse osmosis membrane and collecting a purified sugar liquid from the feed side, while removing fermentation-inhibiting substances from the permeate side, a purified sugar liquid was obtained in the same manner as in Example 1, and the concentrations of fermentation-inhibiting substances and monosaccharides were quantified. The results are summarized in Tables 13 and 14. It was shown by the analysis that, as fermentation-inhibiting substances, acetic acid, formic acid, furfural, HMF, vanillin, acetovanillin and syringic acid were contained. Further, in terms of monosaccharides contained in the respective sugar liquids, glucose and xylose were the major components. Further, although the amounts were very small, arabinose and mannose were also detected.

TABLE 13

Quantification of fermentation-inhibiting substances

| | Aqueous sugar solution | NF membrane-purified sugar liquid | RO membrane-purified sugar liquid |
|---|---|---|---|
| Formic acid | 1.1 g/L | 0 g/L | 0.3 g/L |
| Acetic acid | 2.2 g/L | 0 g/L | 0.2 g/L |
| HMF | 139 mg/L | 1 mg/L | 6 mg/L |
| Furfural | 8 mg/L | 0 mg/L | 3 mg/L |
| Vanillin | 50 mg/L | 1.2 mg/L | 31 mg/L |
| Acetovanillin | 2 mg/L | 0 mg/L | 1 mg/L |
| Syringic acid | 1 mg/L | 0 mg/L | 0 mg/L |

TABLE 14

Quantification of monosaccharides

| | Aqueous sugar solution | NF membrane-purified sugar liquid | RO membrane-purified sugar liquid |
|---|---|---|---|
| Glucose | 2 g/L | 1.8 g/L | 2 g/L |
| Xylose | 15 g/L | 13 g/L | 15 g/L |
| Arabinose | 0.5 g/L | 0.48 g/L | 0.5 g/L |
| Mannose | 0.5 g/L | 0.48 g/L | 0.5 g/L |

The respective purified sugar liquids were confirmed to have largely reduced amounts of fermentation-inhibiting substances compared to the hydrothermally treated liquid obtained in Reference Example 4. On the other hand, since the concentrations of sugars were not largely decreased in the purified sugar liquids, it could be confirmed that processing of the aqueous sugar solution through the NF membrane or RO membrane allows removal of fermentation-inhibiting substances as the permeate, while allowing recovery of a purified sugar liquid, in which the concentrations of fermentation-inhibiting substances are decreased, from the feed side.

Example 6: Step of Filtering Model Sugar Liquids Through Nanofiltration Membrane or Reverse Osmosis Membrane As model sugar liquids for the aqueous sugar solution prepared by hydrolysis of a biomass, one containing sugars at high concentrations (model aqueous sugar solution A) and one containing sugars at low concentrations (model aqueous sugar solution B) were prepared. Their compositions are shown in Tables 15 and 16.

TABLE 15

Compositions of model sugar liquids (monosaccharides)

| | Glucose | Xylose |
|---|---|---|
| Model aqueous sugar solution A | 40 g/L | 20 g/L |
| Model aqueous sugar solution B | 2 g/L | 1 g/L |

TABLE 16

Compositions of model sugar liquids (fermentation-inhibiting substances)

| | Formic acid | Acetic acid | HMF | Furfural | Vanillin |
|---|---|---|---|---|---|
| Model aqueous sugar solution A | 2 g/L | 2 g/L | 1 g/L | 1 g/L | 1 g/L |
| Model aqueous sugar solution B | 2 g/L | 2 g/L | 1 g/L | 1 g/L | 1 g/L |

The pHs of the model sugar liquids A and B were adjusted using sulfuric acid or sodium hydroxide to 0.5, 1, 2, 3, 4, 5, 6 or 7, and the liquids were filtered in the same manner as in Example 1, followed by quantifying the concentrations of fermentation-inhibiting substances and sugars contained in the permeates by the method described in Reference Example 1. The results are shown in Tables 17 to 20. The permeation rates of monosaccharides were different between the model liquids A and B, but not different among the different pHs. Further, the permeation rates of fermentation-inhibiting substances were different among the different pHs, but not different between the model sugar liquids A and B.

TABLE 17

Comparison of permeation rates of sugars through nanofiltration membrane 1

| | Glucose | Xylose |
|---|---|---|
| Model aqueous sugar solution A | 10% | 15% |
| Model aqueous sugar solution B | 3% | 5% |

TABLE 18

Comparison of permeation rates of fermentation-inhibiting substances through nanofiltration membrane at different pHs

| | Formic acid | Acetic acid | HMF | Furfural | Vanillin |
|---|---|---|---|---|---|
| pH 0.5 | Clogging of membrane prevented permeation of liquid | | | | |
| pH 1.0 | 100% | 100% | 98% | 98% | 96% |
| pH 2.0 | 100% | 100% | 98% | 98% | 96% |
| pH 3.0 | 100% | 100% | 98% | 98% | 96% |
| pH 4.0 | 99% | 99% | 98% | 98% | 96% |
| pH 5.0 | 90% | 88% | 98% | 98% | 96% |
| pH 6.0 | 55% | 48% | 100% | 100% | 100% |
| pH 7.0 | 50% | 45% | 100% | 100% | 100% |

TABLE 19

Comparison of permeation rates of sugars through reverse osmosis membrane

| | Glucose | Xylose |
|---|---|---|
| Model aqueous sugar solution A | 0.2% | 0.4% |
| Model aqueous sugar solution B | 0% | 0% |

TABLE 20

Comparison of permeation rates of fermentation-inhibiting substances through reverse osmosis membrane at different pHs

| | Formic acid | Acetic acid | HMF | Furfural | Vanillin |
|---|---|---|---|---|---|
| pH 0.5 | Clogging of membrane prevented permeation of liquid | | | | |
| pH 1.0 | 85% | 55% | 25% | 55% | 15% |
| pH 2.0 | 85% | 52% | 25% | 55% | 15% |

TABLE 20-continued

Comparison of permeation rates of fermentation-inhibiting substances through reverse osmosis membrane at different pHs

|  | Formic acid | Acetic acid | HMF | Furfural | Vanillin |
|---|---|---|---|---|---|
| pH 3.0 | 80% | 50% | 25% | 55% | 15% |
| pH 4.0 | 50% | 25% | 25% | 55% | 15% |
| pH 5.0 | 30% | 15% | 25% | 55% | 15% |
| pH 6.0 | 5% | 0% | 25% | 55% | 15% |
| pH 7.0 | 0% | 0% | 25% | 55% | 15% |

From the above results, it was discovered that either the nanofiltration membrane or reverse osmosis membrane can increase the concentrations of monosaccharides while removing fermentation-inhibiting substances into the filtrate side. Further, it was discovered that the rate of loss of monosaccharides into the filtrate side increases in the nanofiltration membrane in cases where the sugar concentration is high, while loss of sugars hardly occurs in the reverse osmosis membrane even in such cases. Further, it was discovered that the removal rates of organic acids largely vary depending on the pH.

Example 7: Step of Filtering Hydrothermally Treated/Enzyme-Treated Aqueous Sugar Solution Through Reverse Osmosis Membrane (Fouling Suppression Effect by pH Adjustment)

Figure 3:
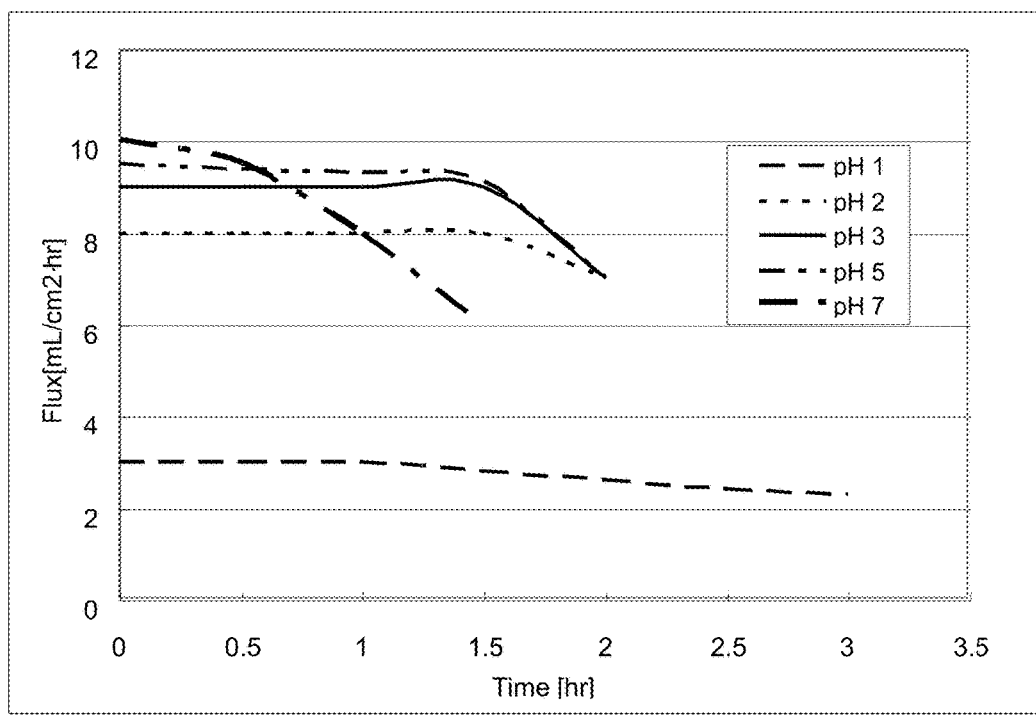
FIG. 3 is a graph showing comparison of the flux quantities at different pHs during filtration of a sugar liquid through a nanofiltration membrane.

The fouling suppression effect by pH adjustment on the aqueous sugar solution obtained in Reference Example 4 was investigated. Ten liters of the aqueous sugar solution obtained in Reference Example 4 was filtered through a microfiltration membrane (manufactured by Millipore; pore size, 0.45 μm; PVDF membrane). The turbidity was not more than 1 NTU at this time. Filtration was further carried out using an ultrafiltration membrane (GE SEPA PW series; polyether sulfone; molecular weight cutoff, 10000). Thereafter, the filtrate was aliquoted into 2-L volumes, and each of these aliquots was prepared with sulfuric acid or ammonia such that the pH became 1, 2, 3, 5 or 7, followed by being filtered through a reverse osmosis membrane in the same manner as in Example 1 until the volume remaining in the raw liquid tank decreased to 0.5 L (4-fold concentration). The amount of flux during the collection of the permeate was calculated based on the differences in the changes in the total amount of the permeate with time. The results of calculation of the flux are shown in FIG. 3. As a result, at a pH of 1, the flux was very small and the filtration took a long time, and, at a pH of 7, remarkable decrease in the flux occurred in the middle of the operation. Also at pHs of 2, 3 and 5, decrease in the flux was observed from about 1.5 hours later, and this was assumed to be due to increase in the sugar concentration, leading to drastic increase in the osmotic pressure. The concentrations of monosaccharides and fermentation-inhibiting substances in the aqueous sugar solution and purified sugar liquids were as shown in Tables 21 and 22, and it could be confirmed that, although monosaccharides were concentrated at the corresponding ratio of concentration, the levels of concentration of the fermentation-inhibiting substances were low, so that removal of the fermentation-inhibiting substances from the aqueous sugar solution could be confirmed.

TABLE 21

Concentrations of monosaccharides

|  | Aqueous sugar solution | Purified sugar liquid (filtration at pH 3) | Purified sugar liquid (filtration at pH 7) |
|---|---|---|---|
| Glucose | 50 g/L | 200 g/L | 200 g/L |
| Xylose | 8 g/L | 32 g/L | 32 g/L |

TABLE 22

Quantification of fermentation-inhibiting substances

|  | Aqueous sugar solution | Purified sugar liquid (filtration at pH 3) | Purified sugar liquid (filtration at pH 7) |
|---|---|---|---|
| Formic acid | 0.1 g/L | 0.2 g/L | 0.4 g/L |
| Acetic acid | 0.5 g/L | 1.2 g/L | 2.0 g/L |
| Furfural | 15 mg/L | 35 mg/L | 35 mg/L |
| HMF | 10 mg/L | 30 mg/L | 30 mg/L |
| Vanillin | 3 mg/L | 9 mg/L | 9 mg/L |
| Acetovanillin | 13 mg/L | 45 mg/L | 45 mg/L |

Example 8: Step of Filtering Hydrothermally Treated Liquid Through Nanofiltration Membrane (Fouling Suppression Effect by Microfiltration Membrane/Ultrafiltration Membrane)

Figure 4:
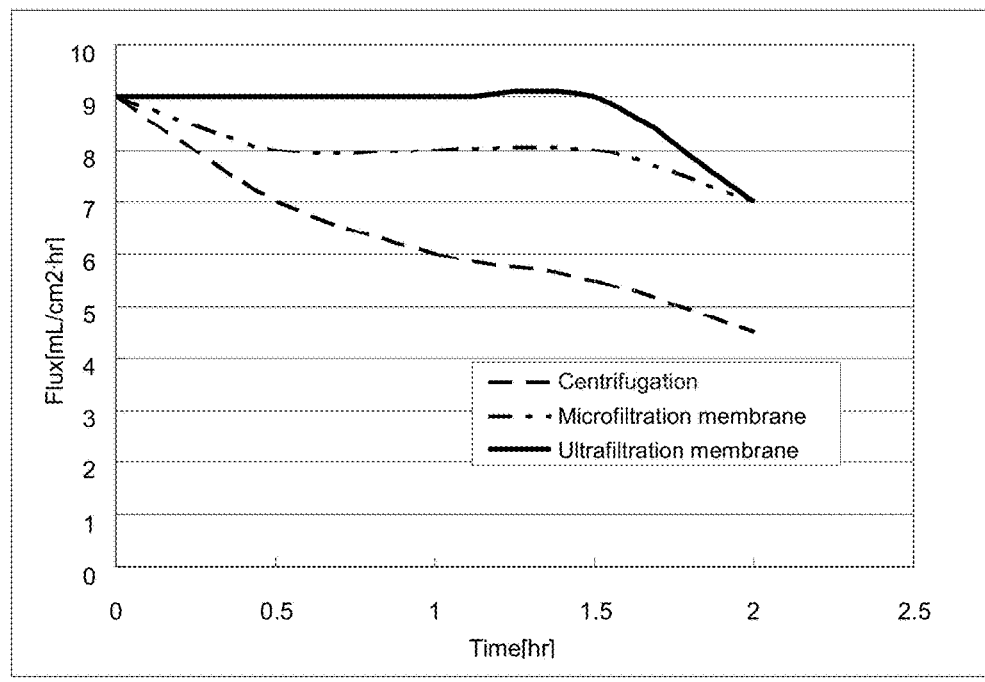
FIG. 4 is a graph showing comparison of the flux quantities by a method wherein a sugar liquid is filtered through a microfiltration membrane or an ultrafiltration membrane, before filtration of the sugar liquid through a nanofiltration membrane.

The fouling suppression effect by filtration treatment, which is carried out before concentration of the hydrothermally treated liquid obtained in Reference Example 4 through a nanofiltration membrane, was investigated by an acceleration test using a reduced volume of the liquid. Three types of liquids, that is, a liquid prepared just by centrifuging the hydrothermally treated liquid obtained in Reference Example 4 as it is, a liquid treated with a microfiltration membrane (manufactured by Millipore; pore size, 0.45 μm; PVDF membrane), and a liquid treated with an ultrafiltration membrane (GE SEPA PW series; polyether sulfone; molecular weight cutoff, 10000), were prepared, and their pHs were adjusted to 3. The turbidity of the centrifugation-treated liquid was 800 NTU, and the turbidities of both of the other 2 types of liquids were not more than 1 NTU. Each liquid in an amount of 2 L was filtered through a nanofiltration membrane in the same manner as in Example 1 until the volume remaining in the raw liquid tank decreased to 0.5 L, and the amount of flux during the collection of the permeate was calculated based on the differences in the changes in the total amount of the permeate with time. The results of calculation of the flux are shown in FIG. 4. As a result, it was shown that, in the case of treatment with only centrifugation, the turbidity was high and the flux drastically decreased during the concentration. It was assumed that this was due to adhesion of components responsible for the turbidity to the membrane during the concentration, resulting in drastic decrease in the filtration capacity of the membrane.

Example 9: Identification of Fouling Components

Figure 5:
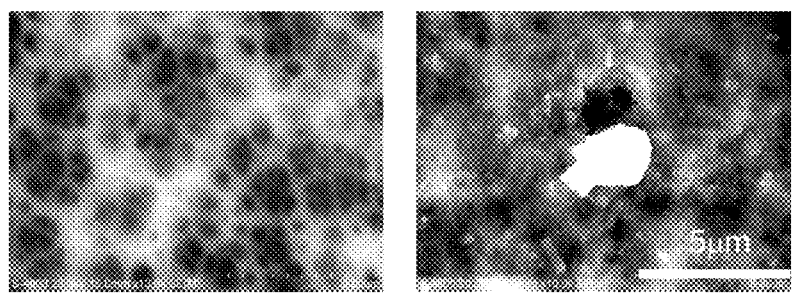
FIG. 5 shows photographs of the membrane surface before and after filtration of a hydrothermally treated liquid through a microfiltration membrane, which photographs were taken under a scanning electron microscope.
Figure 6:
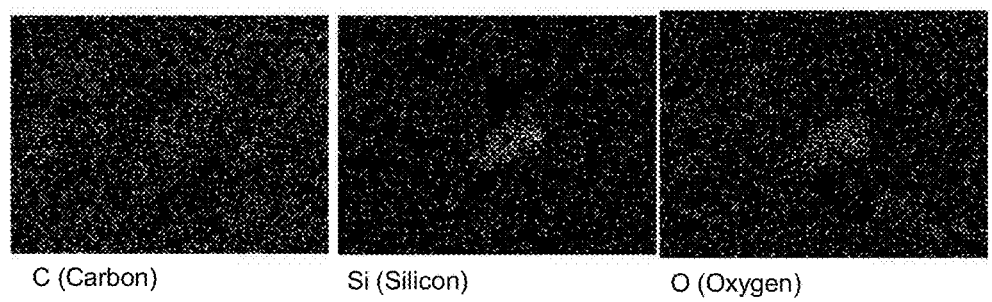
FIG. 6 shows results of measurement of distribution of elements during observation of the scanning electron micrographs shown in FIG. 5, which measurement was carried out with an energy dispersive X-ray analyzer which is attached to the electron scanning microscope.

The hydrothermally treated liquid obtained in Reference Example 4 was aerated and washed, while carrying out microfiltration, and the resulting membrane was dried under vacuum and observed under a scanning electron microscope apparatus (manufactured by Hitachi High-Technologies Corporation, S-4800). Further, component analysis was carried out using an energy dispersive X-ray analyzer (manufactured by HORIBA, Ltd., EX-250) attached to the scanning electron microscope apparatus. As a result, on the microfiltration membrane, many gel deposits and particles having sizes of the order of several nanometers to several micrometers were observed as shown in FIG. 5. These components were subjected to analysis of dispersion of the components, in the mapping mode of the energy dispersive X-ray analyzer, and large quantities of Si (silicon) and O (oxygen) were detected at the positions of the particles (FIG. 6). These particulate matters were assumed to be $SiO_2$ (silica). Further, as the gel components around the particles, C (carbon) and O (oxygen) were observed. Thus, the gel deposits were considered to be undecomposed cellulose, lignin and the like. Further, the filtrate obtained by the microfiltration was filtered through an ultrafiltration membrane, and the ultrafiltration membrane was lightly washed with RO water. The ultrafiltration membrane was then dried under vacuum and subjected to only elementary analysis by an energy dispersive X-ray analyzer using a scanning electron microscope applying a voltage of 20 kV at a magnification of ×100, at 3 different positions. As a result, C (carbon) at a content of 72 to 77% and O (oxygen) at a content of 20 to 25% were detected. Thus, in terms of the removed components, it was assumed that water-soluble polysaccharides, tannin, polyphenol and the like accumulate on the ultrafiltration membrane and removed.

Example 10: Recovery of Enzymes

An example of recovery of enzymes from the aqueous sugar solution obtained in the above Reference Example 1 is described. For the recovery of the enzymes, a polyether sulfone ultrafiltration membrane (diameter, 44.5 mm; Millipore) having a molecular weight cutoff of 10,000 was placed in a Stirred Cells Series 8000 (Millipore), and pressure filtration was carried out using a nitrogen gas cylinder. In the pressure filtration, 50 mL of the sugar liquid obtained in Example 1 was fed to the feed side, and 45 mL of the liquid was removed as a permeate. The enzyme concentration (protein concentration) in 5 mL of the sugar liquid remained in the feed side was measured. The enzyme concentration was colorimetrically measured using BCA measurement kit (BCA Protein Assay Regent kit, manufactured by PIERCE) by measurement of absorbance at 562 nm using bovine albumin (2 mg/mL) as a standard sample. As a result, taking the initial enzyme concentration before the feeding of the liquid as 100%, the enzyme concentration in the liquid recovered in Reference Example 1 could be confirmed to be within the range of 10-60% as a relative value.

Example 11: Changes in Capacity to Remove Fermentation-Inhibiting Substances Depending on Temperature of Aqueous Sugar Solution A step of filtering the ammonia-treated/enzyme-treated aqueous sugar solution obtained in Reference Example 5 through a microfiltration membrane and an ultrafiltration membrane, and then further filtering the solution through a reverse osmosis membrane, followed by recovering a purified sugar solution from the feed side and removing fermentation-inhibiting substances from the permeate side, is described by way of an Example. Through a microfiltration membrane (manufactured by Millipore; pore size, 0.45 μm; PVDF membrane), 4 L of the aqueous sugar solution obtained in Reference Example 5 was filtered. The turbidity was not more than 1 NTU at this time. Filtration was further carried out using an ultrafiltration membrane (GE SEPA G PW series; polyether sulfone; molecular weight cutoff, 10000). This aqueous sugar solution was adjusted with sulfuric acid to pH 3, and a 2-L aliquot of the resulting solution was filtered at an aqueous sugar solution temperature of 25° C. or 50° C. through a reverse osmosis membrane in the same manner as in Example 1 until the volume remaining in the raw liquid tank decreased to 0.5 L, followed by recovering the permeate. Upon completion of the filtration, RO water was added to each liquid to attain a final volume of 2 L, thereby providing a purified sugar liquid. The concentrations of fermentation-inhibiting substances in the purified sugar liquids in the cases of aqueous sugar solution temperatures of 25° C. and 50° C. were as shown in Table 23. The increased temperature of the aqueous sugar solution improved the fermentation-inhibiting substance-removing capacity. This was assumed to be due to increase in the pore size of the membrane caused by the increased temperature of the aqueous sugar solution.

TABLE 23

Changes in fermentation-inhibiting substance-removing capacity depending on temperature of aqueous sugar solution

| | Before treatment of aqueous sugar solution | Treatment of aqueous sugar solution at 25° C. | Treatment of aqueous sugar solution at 50° C. |
| --- | --- | --- | --- |
| Formic acid | 1.1 g/L | 0.6 g/L | 0.2 g/L |
| Acetic acid | 0.5 g/L | 0.3 g/L | 0.1 g/L |
| Furfural | 5 mg/L | 3 mg/L | 1 mg/L |
| Vanillin | 20 mg/L | 16 mg/L | 10 mg/L |
| Acetovanillin | 18 mg/L | 16 mg/L | 12 mg/L |
| Syringic acid | 2 mg/L | 1.9 mg/L | 1.2 mg/L |

Example 12: Changes in Level of Suppression of Loss of Monosaccharides Depending on Temperature of Aqueous Sugar Solution A step of filtering the ammonia-treated/enzyme-treated aqueous sugar solution obtained in Reference Example 5 through a microfiltration membrane and an ultrafiltration membrane, and then further filtering the solution through a nanofiltration membrane, followed by recovering a purified sugar solution from the feed side and removing fermentation-inhibiting substances from the permeate side, is described by way of an Example. Through a microfiltration membrane (manufactured by Millipore; pore size, 0.45 μm; PVDF membrane), 4 L of the aqueous sugar solution obtained in Reference Example 5 was filtered. The turbidity was not more than 1 NTU at this time. Filtration was further carried out using an ultrafiltration membrane (GE SEPA PW series; polyether sulfone; molecular weight cutoff, 10000; manufactured by GE Osmonics). This aqueous sugar solution was adjusted with sulfuric acid to pH 3, and a 2-L aliquot of the resulting solution was filtered at an aqueous sugar solution temperature of 25° C. or 10° C. through a nanofiltration membrane in the same manner as in Example 1 until the volume remaining in the raw liquid tank decreased to 0.5 L, followed by recovering the permeate. Upon completion of the filtration, RO water was added to each liquid to attain a final volume of 2 L, thereby providing a purified sugar liquid. The concentrations of sugars in the purified sugar liquids in the cases of aqueous sugar solution temperatures of 25° C. and 10° C. were as shown in Table 24, indicating that the decreased temperature improved the amount of loss of the sugars. This was assumed to be due to decrease in the pore size of the membrane caused by the decreased temperature of the aqueous sugar solution.

TABLE 24

Loss of sugars depending on temperature of aqueous sugar solution

|  | Before treatment of aqueous sugar solution | Treatment of aqueous sugar solution at 25° C. | Treatment of aqueous sugar solution at 10° C. |
|---|---|---|---|
| Glucose | 50 g/L | 44 g/L | 50 g/L |
| Xylose | 25 g/L | 21 g/L | 25 g/L |
| Arabinose | 2 g/L | 1.8 g/L | 2 g/L |
| Mannose | 1 g/L | 0.8 g/L | 1 g/L |

Example 13: Production Examples of Purified Sugar Liquids Using Various Nanofiltration Membranes The aqueous sugar solution obtained in Reference Example 3 was further filtered through a microfiltration membrane (manufactured by Millipore; pore size, 0.05 μm; PVDF membrane), and 20 L of a solution prepared by 20-fold diluting the aqueous sugar solution with RO water was treated with a nanofiltration membrane until the volume of the solution decreased to 1 L in the same manner as in Example 1. As 90φ nanofiltration membranes, a cross-linked piperazine polyamide nanofiltration membrane UTC60 (nanofiltration membrane 1, manufactured by TORAY INDUSTRIES, INC.), a cross-linked piperazine polyamide nanofiltration membrane NF-400 (nanofiltration membrane 2, manufactured by Filmtec Corporation), a polyamide nanofiltration membrane NF99 (nanofiltration membrane 3, manufactured by Alfa-Laval) and a cellulose acetate nanofiltration membrane GE Sepa DK (nanofiltration membrane 4, manufactured by GE Osmonics) were used. The permeation rates of fermentation-inhibiting substances (acetic acid, formic acid, HMF, furfural, vanillin, acetovanillin, syringic acid and levulinic acid) and the permeation rates of monosaccharides (glucose and xylose) contained in the permeate were calculated. The results indicated that the monosaccharides and the fermentation-inhibiting substances could be blocked with any of the nanofiltration membranes, and that, in particular, the nanofiltration membranes 1 to 3, that is, the polyamide nanofiltration membrane and the cross-linked piperazine polyamide nanofiltration membranes, have low permeation rates of monosaccharides, while having high permeation rates of fermentation-inhibiting substances (Tables 25 and 26).

TABLE 26

Comparison of permeation rates of monosaccharides through various nanofiltration membranes

|  | Glucose | Xylose |
|---|---|---|
| Nanofiltration membrane 1 | 0.8% | 1.2% |
| Nanofiltration membrane 2 | 1.15% | 2.0% |
| Nanofiltration membrane 3 | 1.09% | 1.89% |
| Nanofiltration membrane 4 | 2.16% | 4.5% |

Example 14: Production Examples of Purified Sugar Liquids Using Various Reverse Osmosis Membranes The aqueous sugar solution obtained in Reference Example 5 was filtered through a microfiltration membrane (manufactured by Millipore; pore size, 0.45 μm; PVDF membrane). The turbidity was not more than 1 NTU at this time. Filtration was further carried out using an ultrafiltration membrane (GE SEPA PW series; polyether sulfone; molecular weight cutoff, 10000). The filtrate was adjusted with sulfuric acid to pH 3, and 20-L aliquots of the resulting liquid were treated in the same manner as in Example 1 with reverse osmosis membranes. As the reverse osmosis membranes, a cross-linked wholly aromatic polyamide reverse osmosis membrane UTC80 (reverse osmosis membrane 1, manufactured by TORAY INDUSTRIES, INC.), a membrane prepared by soaking the cross-linked wholly aromatic polyamide reverse osmosis membrane UTC80 in a cellulase enzyme liquid Novozyme 188 (*Aspergillus niger*-derived β-glucosidase preparation, Sigma Aldrich Japan) at 50° C. for 1 day and washing the resulting membrane with RO water (reverse osmosis membrane 2), a polyamide reverse osmosis membrane DESAL-3B (reverse osmosis membrane 3; manufactured by DESAL), a cellulose acetate reverse osmosis membrane GE SEPA CE (reverse osmosis membrane 4, manufactured by GE Osmonics) (Comparative Example), and a membrane prepared by soaking the cellulose acetate reverse osmosis membrane GE SEPA CE (manufactured by GE Osmonics) in a cellulase enzyme liquid Novozyme 188 (*Aspergillus niger*-derived β-glucosidase preparation, Sigma Aldrich Japan) at 50° C. for 1 day and washing the resulting membrane with RO water (reverse osmosis membrane 5) were used, and each permeate was recovered until the volume of the raw liquid decreased to one fourth of the initial volume.

TABLE 25

Comparison of permeation rates of fermentation-inhibiting substances through various nanofiltration membranes

|  | Formic Acid | Acetic acid | HMF | Furfural | Vanillin | Acetovanillin | Syringic acid | Levulinic acid |
|---|---|---|---|---|---|---|---|---|
| Nanofiltration membrane 1 | 99% | 99% | 98% | 98% | 99% | 99% | 99% | 99% |
| Nanofiltration membrane 2 | 99% | 99% | 97% | 97% | 99% | 99% | 99% | 99% |
| Nanofiltration membrane 3 | 99% | 99% | 98% | 98% | 99% | 99% | 99% | 99% |
| Nanofiltration membrane 4 | 99% | 97% | 94% | 94% | 97% | 97% | 99% | 99% |

RO water in the same amount as the permeate was fed to the concentrated liquid in the raw liquid tank, and the concentrations of fermentation-inhibiting substances contained in the raw liquid tank and the permeate were analyzed by HPLC (manufactured by Shimadzu Corporation), thereby calculating the permeation rates of the fermentation-inhibiting substances (acetic acid, formic acid, HMF, furfural, vanillin, acetovanillin and syringic acid) and the permeation rates of the monosaccharides (glucose and xylose). The results indicated that the monosaccharides and the fermentation-inhibiting substances could be blocked with any of the reverse osmosis membranes, and that, in particular, the reverse osmosis membranes 1 and 2, that is, the polyamide and cross-linked wholly aromatic polyamide reverse osmosis membranes, have low permeation rates of monosaccharides, while having high permeation rates of fermentation-inhibiting substances. It was further revealed that the cellulose acetate membranes are less resistant to the cellulase (Tables 27 and 28).

turbidity was not more than 0.5 NTU at this time. The filtrate was divided into 3 aliquots (20 L each), and treated with only a nanofiltration membrane until the volume in the raw liquid side decreased to 5 L (4-fold concentration); treated with a nanofiltration membrane until the volume in the raw liquid side decreased to 10 L (2-fold concentration), followed by treatment with a reverse osmosis membrane until the volume in the raw liquid side decreased to 5 L (additional 2-fold concentration: a total of 4-fold concentration), or treated with only a reverse osmosis membrane until the volume in the raw liquid side decreased to 5 L (4-fold concentration); in the same manner as in Example 7. As the nanofiltration membrane, a cross-linked piperazine polyamide nanofiltration membrane UTC60 (nanofiltration membrane 1, manufactured by TORAY INDUSTRIES, INC.) was used, and, as the reverse osmosis membrane, a cross-linked wholly aromatic polyamide reverse osmosis membrane UTC80 (reverse osmosis membrane 1, manufactured by TORAY INDUSTRIES, INC.) was used.

TABLE 27

Comparison of permeation rates of fermentation-inhibiting substances through various reverse filtration membranes

| | Acetic acid | Formic acid | HMF | Furfural | Vanillin | Acetovanillin | Syringic acid |
|---|---|---|---|---|---|---|---|
| Reverse osmosis membrane 1 | 50% | 80% | 25% | 55% | 15% | 10% | 10% |
| Reverse osmosis membrane 2 | 50% | 80% | 25% | 55% | 15% | 10% | 10% |
| Reverse osmosis membrane 3 | 45% | 75% | 20% | 55% | 15% | 10% | 10% |
| Reverse osmosis membrane 4 | 30% | 50% | 5% | 15% | 5% | 0% | 0% |
| Reverse osmosis membrane 5 | 99% | 99% | 99% | 99% | 95% | 92% | 85% |

TABLE 28

Comparison of permeation rates of monosaccharides through various reverse osmosis filtration membranes

| | Glucose | Xylose |
|---|---|---|
| Reverse osmosis membrane 1 | 0.1% | 0% |
| Reverse osmosis membrane 2 | 0.1% | 0% |
| Reverse osmosis membrane 3 | 0.2% | 0.1% |
| Reverse osmosis membrane 4 | 1.0% | 2.0% |
| Reverse osmosis membrane 5 | 75% | 85% |

Example 15: Comparison of Effects to Concentrate Monosaccharides and Fermentation-Inhibiting Substances To compare the effects to concentrate monosaccharides and fermentation-inhibiting substances, the degrees of concentration of monosaccharides and fermentation-inhibiting substances were compared among cases of filtration of the aqueous sugar solution through a nanofiltration membrane and/or reverse osmosis membrane. After preparing 60 L of the ammonia-treated/enzyme-treated aqueous sugar solution obtained in Reference Example 5 to pH 3 with aqueous ammonia and sulfuric acid, the resulting solution was filtered through a microfiltration membrane. The solution was further filtered through an ultrafiltration membrane. The Table 29 shows the results of analysis of the concentrations of monosaccharides and fermentation-inhibiting substances contained in the purified sugar liquid, which analysis was carried out by HPLC under the conditions shown in Reference Example 1. Below each of the concentrations shown in the table, the concentration expected when the liquid is diluted later such that a glucose concentration of 50 g/L is attained is shown. As a result, it was revealed that the degrees of concentration of the fermentation-inhibiting substances were lower than the degrees of concentration of the monosaccharides, and that the fermentation-inhibiting-substance-removing performance per unit glucose concentration was highest in the case of the nanofiltration membrane treatment, followed by the case of the nanofiltration membrane treatment and the subsequent reverse osmosis membrane treatment, and the case of the reverse osmosis membrane treatment, in that order. On the other hand, by using the nanofiltration membrane and the reverse osmosis membrane in combination, loss of sugars into the filtrate side of a nanofiltration membrane, which remarkably occurs in cases where the sugar concentration is as high as not less than 100 g/L, could be reduced, and the fermentation-inhibiting-substance-removing performance was largely improved compared to the case of treatment only with a reverse osmosis membrane.

TABLE 29

Quantification of monosaccharides and fermentation-inhibiting substances

| | Aqueous sugar solution | NF membrane-Treated | NF membrane/RO membrane-treated | RO membrane-treated |
|---|---|---|---|---|
| Glucose | 50 g/L | 160 g/L (50 g/L) | 195 g/L (50 g/L) | 200 g/L (50 g/L) |
| Xylose | 25 g/L | 79 g/L (25 g/L) | 96 g/L (50 g/L) | 100 g/L (50 g/L) |
| Arabinose | 2 g/L | 6 g/L (1.9 g/L) | 7.6 g/L (1.9 g/L) | 8 g/L (2 g/L) |
| Mannose | 1 g/L | 3.0 g/L (0.9 g/L) | 3.2 g/L (0.9 g/L) | 3.8 g/L (1 g/L) |
| Formic acid | 1.1 g/L | 1.0 g/L (0.3 g/L) | 1.3 g/L (0.3 g/L) | 2.0 g/L (0.5 g/L) |
| Acetic acid | 0.5 g/L | 0.4 g/L (0.1 g/L) | 0.7 g/L (0.2 g/L) | 1.2 g/L (0.3 g/L) |
| HMF | 0 mg/L | 0 mg/L (0 mg/L) | 0 mg/L (0 mg/L) | 0 mg/L (0 mg/L) |
| Furfural | 5 mg/L | 4 mg/L (1.3 mg/L) | 7 mg/L (1.8 mg/L) | 12 mg/L (3 mg/L) |
| Vanillin | 20 mg/L | 18 mg/L (5.6 mg/L) | 30 mg/L (7.7 mg/L) | 60 mg/L (15 mg/L) |
| Acetovanillin | 18 mg/L | 18 mg/L (5.6 mg/L) | 26 mg/L (6.7 mg/L) | 70 mg/L (17 mg/L) |
| Syringic acid | 2 mg/L | 2 mg/L (0.6 mg/L) | 4 mg/L (1.0 mg/L) | 8 mg/L (2.0 mg/L) |

Example 16: Production Examples of Purified Sugar Liquids Using Low-pressure/Ultralow-Pressure Type Reverse Osmosis Membranes To compare the effects to concentrate monosaccharides and fermentation-inhibiting substances among different types of reverse osmosis membranes, a model sugar liquid was filtered through reverse osmosis membranes having different permeation flow rates in the same manner as in Example 6. The compositions of model sugar liquids of the aqueous sugar solution prepared by hydrolysis of biomass are shown in Table 30.

TABLE 30

Composition of model sugar liquid

| | Glucose | Xylose | Acetic acid |
|---|---|---|---|
| Model aqueous sugar solution | 40 g/L | 20 g/L | 2 g/L |

As the reverse osmosis membranes, BW-30 manufactured by Filmtec Corporation (reverse osmosis membrane 6) and SU-700 manufactured by TORAY INDUSTRIES, INC. (reverse osmosis membrane 7), which are low-pressure type membranes; TFC-ULP manufactured by KOCH (reverse osmosis membrane 8) and SUL-G10 manufactured by TORAY INDUSTRIES, INC. (reverse osmosis membrane 9), which are ultralow-pressure type membranes; and DESAL-3B manufactured by DESAL (reverse osmosis membrane 10), which is a medium-pressure type membrane for reference; were used. The permeation flow rates of sodium chloride (500 mg/L) per unit membrane area ($m^3/m^2/day$) observed at a filtration pressure of 0.75 MPa at pH 6.5 for the respective membranes are shown in Table 31.

TABLE 31

Values of permeation flow rates of respective reverse osmosis membranes

| | Permeation flow rate ($m^3/m^2/D$) |
|---|---|
| Reverse osmosis membrane 6 | 0.51 |
| Reverse osmosis membrane 7 | 0.51 |
| Reverse osmosis membrane 8 | 0.9 |
| Reverse osmosis membrane 9 | 0.8 |
| Reverse osmosis membrane 10 | 0.27 |

Model sugar liquids A and B whose pHs were adjusted with sulfuric acid or sodium hydroxide to 2, 3, 4, 5, 6 or 7 were filtered in the same manner as in Example 1, and the concentrations of acetic acid, which is a fermentation-inhibiting substance, and sugars contained in the permeate were quantified by the method described in Reference Example 1. The results are shown in Tables 32 and 33. The permeation rate of acetic acid varied depending on the pH, and the loss of sugars tended to be smaller in the low-pressure type than in the ultralow-pressure type, although the difference was very small. From these results, it was revealed that low-pressure/ultralow-pressure type reverse osmosis membranes are excellent in the performance of removal of organic acids and can efficiently remove fermentation-inhibiting substances even in cases where the pH of the raw liquid is higher than 3.

TABLE 32

Comparison of permeation rates of acetic acid through respective reverse osmosis membranes at different pHs

| | Reverse osmosis membrane 6 | Reverse osmosis membrane 7 | Reverse osmosis membrane 8 | Reverse osmosis membrane 9 | Reverse osmosis membrane 10 |
|---|---|---|---|---|---|
| pH 2.0 | 78% | 80% | 99% | 99% | 45% |
| pH 3.0 | 60% | 65% | 82% | 78% | 45% |

TABLE 32-continued

Comparison of permeation rates of acetic acid through respective reverse osmosis membranes at different pHs

| | Reverse osmosis membrane 6 | Reverse osmosis membrane 7 | Reverse osmosis membrane 8 | Reverse osmosis membrane 9 | Reverse osmosis membrane 10 |
|---|---|---|---|---|---|
| pH 4.0 | 45% | 50% | 60% | 58% | 25% |
| pH 5.0 | 20% | 20% | 35% | 33% | 15% |
| pH 6.0 | 5% | 5% | 10% | 10% | 0% |
| pH 7.0 | 0% | 0% | 5% | 5% | 0% |

TABLE 33

Comparison of permeation rates of sugars through respective reverse osmosis membranes

| | Glucose | Xylose |
|---|---|---|
| Reverse osmosis membrane 6 | 0.5% | 0.5% |
| Reverse osmosis membrane 7 | 0.5% | 0.5% |
| Reverse osmosis membrane 8 | 1.0% | 1.2% |
| Reverse osmosis membrane 9 | 0.8% | 1.0% |
| Reverse osmosis membrane 10 | 0.2% | 0.1% |

Production methods of chemical products using the purified sugar liquid as a fermentation feedstock are now described in more detail by way of Examples for L-lactic acid, D-lactic acid, ethanol, cadaverine and succinic acid. However, the chemical products produced by our method are not restricted to the Examples below.

Reference Example 6: Methods for Measuring Concentrations of Chemical Products L-Lactic Acid, D-Lactic Acid The concentration of accumulated L-lactic acid or D-lactic acid was confirmed by measuring the amount of lactic acid by the HPLC method:
Column: Shim-Pack SPR-H (manufactured by Shimadzu Corporation)
Mobile phase: 5 mM p-toluenesulfonic acid (flow rate, 0.8 mL/min.)
Reaction solution: 5 mM p-toluenesulfonic acid, 20 mM Bis-Tris, 0.1 mM EDTA-2Na (flow rate, 0.8 mL/min.)
Detection method: electric conductivity
Temperature: 45° C.
Further, the optical purity of L-lactic acid was measured by the HPLC method under the following conditions:
Column: TSK-gel Enantio L1 (manufactured by Tosoh Corporation)
Mobile phase: 1 mM aqueous copper sulfate solution
Flow rate: 1.0 mL/min.
Detection method: UV 254 nm
Temperature: 30° C.
Further, the optical purity of L-lactic acid was calculated by the following equation:

Optical purity(%)=100×(L−D)/(L+D).

In this equation, L represents the concentration of L-lactic acid, and D represents the concentration of D-lactic acid. The optical purity of D-lactic acid was also similarly calculated.
Ethanol
The concentration of accumulated ethanol was quantified by the gas chromatography method. The evaluation was carried out by detection/calculation using a Shimadzu GC-2010 capillary GC TC-1 (GL science) 15 meter L.×0.53 mm I.D., df 1.5 μm with a hydrogen flame ionization detector.
Cadaverine
Cadaverine was evaluated by the following HPLC method:
Column used: CAPCELL PAK C18 (manufactured by Shiseido Co., Ltd.)
Mobile phase: 0.1% (w/w) aqueous phosphoric acid solution:acetonitrile=4.5:5.5
Detection: UV 360 nm
Sample pretreatment: To 25 μL of the sample to be analyzed, 25 μL of 1,4-diaminobutane (0.03 M), 150 μL of sodium hydrogen carbonate (0.075 M) and a solution of 2,4-dinitrofluorobenzene (0.2 M) in ethanol were added as internal standards, and the resulting mixture was incubated at 37° C. for 1 hour.
In 1 mL of acetonitrile, 50 μL of the above reaction solution was dissolved, and the resulting solution was centrifuged at 10,000 rpm for 5 minutes, followed by analyzing 10 μL of the supernatant by HPLC.
Succinic Acid
Measurement of the concentration of accumulated succinic acid was carried out by analysis using HPLC (manufactured by Shimadzu Corporation; LC10A; RI monitor: RID-10A; column: Aminex HPX-87H). The column temperature was set to 50° C. After equilibrating the column with 0.01 N $H_2SO_4$, the sample was injected, and elution was carried out with 0.01 N $H_2SO_4$ to perform the analysis.

Figure 7:
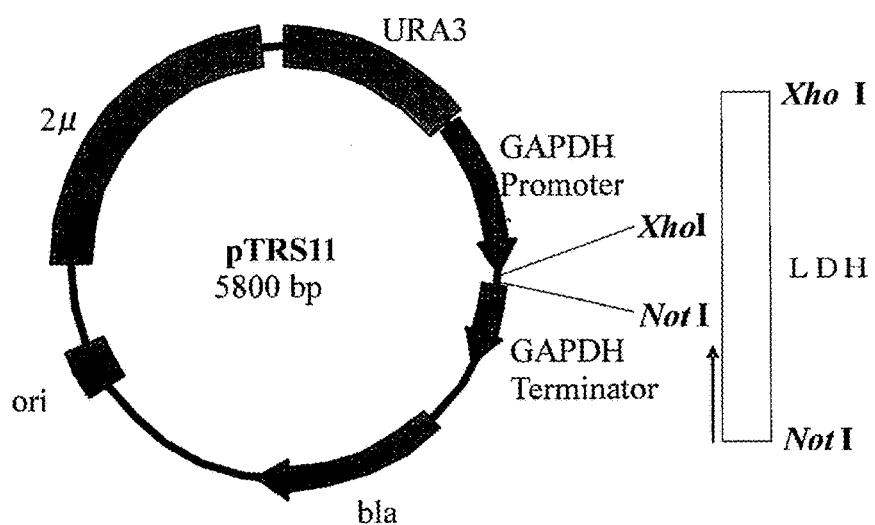
FIG. 7 is a diagram showing a physical map of a yeast expression vector pTRS11.

Reference Example 7: Preparation of Yeast Strain Having Ability to Produce L-Lactic Acid A yeast strain having an ability to produce L-lactic acid was prepared as follows. By linking a human-derived LDH gene in the downstream of the PDC1 promoter in the yeast genome, a yeast strain having an ability to produce L-lactic acid was prepared. The polymerase chain reaction (PCR) was carried out using La-Taq (manufactured by TAKARA BIO INC.) or KOD-Plus-polymerase (manufactured by Toyobo Co. Ltd.) according to the attached instructions.
A human breast cancer cell line (MCF-7) was cultured, and the cultured cells were collected, followed by extracting RNA using TRIZOL Reagent (manufactured by INVITROGEN) and carrying out reverse transcription reaction using the obtained RNA as a template and SuperScript Choice System (manufactured by INVITROGEN), thereby synthesizing cDNA. For details of the respective operations, the manufacturer's instructions were followed. The obtained cDNA was used as a template for the subsequent amplification by PCR.
Using the cDNA obtained by the above operations as a template for amplification, oligonucleotides having the sequences shown in SEQ ID NO:1 and SEQ ID NO:2 as a primer set, and KOD-Plus-polymerase (manufactured by Toyobo Co. Ltd.), PCR was carried out to clone the L-ldh gene. Each PCR-amplified fragment was purified, and phosphorylated at its ends with T4 Polynucleotide Kinase (manufactured by TAKARA BIO INC.), followed by ligation into pUC118 vector (which had been digested with the restriction enzyme HindIII and dephosphorylated at the site of cleavage). The ligation was carried out using DNA Ligation Kit Ver. 2 (manufactured by TAKARA BIO INC.). E. coli DH5α was transformed with the ligation plasmid products, and the plasmid DNAs were recovered to obtain plasmids wherein various L-ldh genes (SEQ ID NO:3) are subcloned. The obtained pUC118 plasmids wherein the L-ldh genes are inserted were digested with the restriction enzymes XhoI and NotI to obtain DNA fragments, each of which was then inserted into the XhoI/NoI-restriction site of the yeast expression vector pTRS11 (FIG. 7). Thus, the human-derived L-ldh gene-expressing plasmid pL-ldh5 (L-ldh gene) was obtained. The above-described pL-ldh5, which is a human-derived L-ldh gene-expressing plasmid, was deposited with International Patent Organism Depositary, National Institute of Advanced Industrial Science and Technology (AIST Tsukuba Central 6, 1-1-1 Higashi, Tsukuba, Ibaraki, Japan) under the accession No. FERM AP-20421 (date of deposit: Feb. 21, 2005) in the form of the plasmid itself.

Using the plasmid pL-ldh5 containing the human-derived LDH gene as a template for amplification, and oligonucleotides having the sequences shown in SEQ ID NO:4 and SEQ ID NO:5 as a primer set, PCR was carried out to amplify a DNA fragment containing the human-derived LDH gene having a length of 1.3 kb and the terminator sequence of a Saccharomyces cerevisiae-derived TDH3 gene. Further, using the plasmid pRS424 as a template for amplification, and oligonucleotides having the sequences shown in SEQ ID NO:6 and SEQ ID NO:7 as a primer set, PCR was carried out to amplify a DNA fragment containing a Saccharomyces cerevisiae-derived TRP1 gene having a length of 1.2 kb. Each DNA fragment was separated by 1.5% agarose gel electrophoresis and purified according to a conventional method. Using a mixture of the thus obtained 1.3-kb fragment and 1.2-kb fragment as a template for amplification, and oligonucleotides having the sequences shown in SEQ ID NO:4 and SEQ ID NO:7 as a primer set, PCR was carried out to obtain a product, which was then subjected to 1.5% agarose gel electrophoresis, thereby preparing a DNA fragment having a length of 2.5 kb in which the human-derived LDH gene and TRP1 gene are linked. With this DNA fragment having a length of 2.5 kb, the budding yeast Saccharomyces cerevisiae NBRC10505 strain was transformed to tryptophan prototrophy according to a conventional method.

Confirmation of the fact that the obtained transformed cells have the human-derived LDH gene linked to the downstream of the PDC1 promoter in the yeast genome was carried out as follows. The genomic DNA of the transformed cells was prepared according to a conventional method, and PCR was then carried out using the prepared genomic DNA as a template for amplification, and oligonucleotides having the sequences shown in SEQ ID NO:8 and SEQ ID NO:9 as a primer set, to confirm whether an amplified DNA fragment having a length of 0.7 kb was obtained. Further, whether or not the transformed cells have an ability to produce lactic acid was confirmed by culturing the transformed cells in SC medium (METHODS IN YEAST GENETICS 2000 EDITION, CSHL PRESS) and confirming whether or not the culture supernatant contained lactic acid by measuring the amount of lactic acid by the HPLC method.

By the HPLC analysis, L-lactic acid at a concentration of 4 g/L was detected, and the concentration of D-lactic acid was under the detection limit. From the above studies, it was confirmed that this transformant has an ability to produce L-lactic acid. The obtained transformed cells were designated the yeast SW-1 strain, and this strain was used for the subsequent L-lactic acid fermentation.

Reference Example 8: L-Lactic Acid Fermentation (Yeast)

L-lactic acid fermentation was carried out using the yeast strain obtained in Reference Example 7 (SW-1). To the medium, glucose as a carbon source, and Yeast Synthetic Drop-out Medium Supplement Without Tryptophan (Sigma Aldrich Japan, Table 34, Drop-out MX), Yeast Nitrogen Base w/o Amino Acids and Ammonium Sulfate (Difco, Yeast NTbase), and ammonium sulfate, as the other components, were blended at the ratio shown in Table 34. The medium was subjected to sterilization by filtration (Millipore, Stericup 0.22 μm) before being used in the fermentation. The concentration of glucose was quantified using Glucose Test Wako (manufactured by Wako Pure Chemical Industries, Ltd.). The amount of lactic acid produced in each culture was measured by HPLC under the same conditions as in Reference Example 6.

TABLE 34

| Composition of L-lactic acid fermentation medium | |
|---|---|
| Composition | Concentration of component |
| Glucose | 50 g/L |
| Drop-out MX | 3.8 g/L |
| Yeast NTbase | 1.7 g/L |
| Ammonium sulfate | 5 g/L |

The SW-1 strain was cultured in 5 mL of a fermentation medium (preculture medium) in a test tube with shaking overnight (preculture). Yeast cells were collected from the preculture by centrifugation, and the cells were washed well with 15 mL of sterile water. The washed yeast cells were inoculated to 100 mL the media having the compositions described in Table 34, and cultured in a 500-mL Sakaguchi flask for 40 hours with shaking (main culture).

Reference Example 9: Method of L-Lactic Acid Fermentation (Lactic Acid Bacterium)

The L-lactic acid bacterium fermentation medium shown in Table 35 was autoclaved (121° C., 15 minutes) and used as the medium. As the lactic acid bacterium, the Lactococcus lactis JCM 7638 strain, which is a prokaryotic microorganism, was used, and, as the medium, the lactic acid bacterium lactic acid fermentation medium having the composition shown in Table 35 was used. L-lactic acid contained in the fermentation liquid was evaluated by the same method as in Reference Example 1. The concentration of glucose was measured using Glucose Test Wako C (manufactured by Wako Pure Chemical Industries, Ltd.).

TABLE 35

Lactic acid bacterium lactic acid fermentation medium

| Composition | Concentration of component |
|---|---|
| Glucose | 50 g/L |
| Yeast extract | 5 g/L |
| Polypeptone | 5 g/L |
| Sodium chloride | 5 g/L |

The *Lactococcus lactis* JCM 7638 strain was subjected to static culture in 5 mL of the nitrogen-purged lactic acid fermentation medium shown in Table 35 placed in a test tube, for 24 hours at a temperature of 37° C. (preculture). The obtained culture was inoculated to 50 mL of a fresh nitrogen-purged lactic acid fermentation medium, and subjected to static culture for 48 hours at a temperature of 37° C. (main culture).

Reference Example 10: Ethanol Fermentation (Yeast)

Ethanol fermentation by a yeast strain (OC2, *Saccharomyces cerevisiae*, wine yeast) was studied. The medium to be used for the fermentation was prepared by subjecting the medium having the composition of Reference Example 8 to sterilization by filtration (Millipore, Stericup 0.22 μm). The concentration of glucose was quantified using Glucose Test Wako (manufactured by Wako Pure Chemical Industries, Ltd.). The amount of ethanol produced in each culture was measured by GC under the same conditions as in Reference Example 7.

The OC2 strain was cultured in 5 mL of a fermentation medium (preculture medium) in a test tube with shaking overnight (preculture). Yeast cells were recovered from the preculture by centrifugation, and the cells were washed well with 15 mL of sterile water. The washed yeast cells were inoculated to 100 mL media having the compositions described in Table 34, and cultured in a 500-mL Sakaguchi flask for 24 hours with shaking (main culture).

Reference Example 11: Cadaverine Fermentation (*Corynebacterium glutamicum*)

As a microorganism for production of cadaverine, the *Corynebacterium glutamicum* TR-CAD1 strain described in JP 2004-222569 A was used, to study cadaverine fermentation by glucose assimilation. A cadaverine fermentation medium was prepared by preparing a sugar liquid such that the glucose composition shown in Table 36, as a carbon source, was attained and a pH of 7.0 was attained with 3 M aqueous ammonia. Evaluation of the concentration of cadaverine, which is the product, was carried out by measurement by the HPLC method. The concentration of glucose was measured using Glucose Test Wako C (manufactured by Wako Pure Chemical Industries, Ltd.).

TABLE 36

Cadaverine fermentation medium

| Composition | Concentration of component |
|---|---|
| Glucose | 50 g/L |
| Citric acid | 1 g/L |
| Urea | 15 g/L |
| Potassium dihydrogenphosphate | 0.5 g/L |
| Dipotassium hydrogenphosphate | 0.5 g/L |
| Magnesium sulfate heptahydrate | 0.5 g/L |
| L-threonine | 0.8 g/L |
| L-methionine | 0.6 g/L |
| L-leucine | 1.5 g/L |
| Iron sulfate heptahydrate | 6.0 mg/L |
| Manganese sulfate monohydrate | 4.2 mg/L |
| Biotin | 1.0 mg/L |
| Thiamine | 2.0 mg/L |

In a test tube, 5 mL of the cadaverine fermentation medium supplemented with kanamycin (25 μg/mL) was added to the *Corynebacterium glutamicum* TR-CAD1 strain, and the strain was cultured overnight with shaking (preculture). From the preculture, the *Corynebacterium glutamicum* TR-CAD1 strain was recovered by centrifugation, and the cells were washed well with 15 mL of sterile water. The washed bacterial cells were inoculated to 100 mL of the above-described medium, and cultured in a 500-mL Sakaguchi flask for 24 hours with shaking (main culture).

Reference Example 12: D-Lactic Acid Fermentation

As the microorganism, the yeast NBRC10505/pTM63 strain described in JP 2007-074939 A was used, and, as the medium, the D-lactic acid production medium having the composition shown in Table 37 was used. Evaluation of the concentration of D-lactic acid, which is the product, was carried out by measurement by the HPLC method in the same manner as in Reference Example 1. The concentration of glucose was measured using Glucose Test Wako C (manufactured by Wako Pure Chemical Industries, Ltd.).

TABLE 37

D-Lactic acid fermentation medium

| Composition | Concentration of component |
|---|---|
| Glucose | 50 g/L |
| Yeast Nitrogen base w/o amino acid | 6.7 g/L |
| Nineteen standard amino acids excluding leucine | 152 mg/L |
| Leucine | 760 mg/L |
| Inositol | 152 mg/L |
| p-Aminobenzoic acid | 16 mg/L |
| Adenine | 40 mg/L |

The NBRC10505/pTM63 strain was cultured in 5 mL of the D-lactic acid production medium in a test tube overnight with shaking (preculture). The obtained culture was inoculated to 50 mL of a fresh D-lactic acid production medium, and cultured in a 500-mL Sakaguchi flask for 24 hours at a temperature of 30° C. with shaking (main culture).

Reference Example 13: Method of Succinic Acid Fermentation

As a microorganism having an ability to produce succinic acid, the *Anaerobiospirillum succiniciproducens* ATCC53488 strain was used, to carry out succinic acid fermentation. In a 125-mL Erlenmeyer flask, 100 mL of the seed culture medium having the composition shown in Table 38 was placed, followed by heat sterilization.

TABLE 38

Succinic acid fermentation medium

| Composition | Concentration of component |
|---|---|
| Glucose | 50 g/L |
| Polypeptone | 10 g/L |
| Yeast extract | 5 g/L |
| Dipotassium hydrogenphosphate | 1 g/L |
| Sodium chloride | 1 g/L |
| Magnesium chloride | 0.2 g/L |

In an anaerobic glove box, 1 mL of 30 mM $Na_2CO_3$ and 0.15 mL of 180 mM $H_2SO_4$ were added to the medium, and further, 0.5 mL of a reducing solution containing 0.25 g/L cysteine.HCl and 0.25 g/L $Na_2S$ was added thereto, followed by inoculation of the ATCC53488 strain and static culture at 39° C. for 24 hours (main culture).

Example 17: Fermentation for Producing Chemical Products Using Sugar Liquids Purified from Dilute Sulfuric Acid-Treated/Enzyme-Treated Aqueous Sugar Solution From 1 liter each of the aqueous sugar solution and the purified sugar liquids (nanofiltration membrane-treated liquid and reverse osmosis membrane-treated liquid) in Example 1, water was evaporated under reduced pressure (200 hPa) using a rotary evaporator (manufactured by Tokyo Rikakikai) to obtain an about 3-fold concentrated solution/liquid. Using these and, for comparison, reagent grade glucose, medium components suitable for the respective cases of fermentation under the concentration conditions of the respective medium components described in the fermentation conditions shown in Reference Examples 8 to 13 were prepared, and the prepared medium components were used in the main culture. In the preculture, reagent grade glucose was used, and each sugar liquid was used only in the main culture. As a result, as shown in Table 39, the cases in which the membrane treatment was carried out showed better suppression of fermentation inhibition and improved concentrations of chemical products accumulated, compared to the case in which membrane treatment was not carried out.

TABLE 39

Concentrations of chemical products accumulated

| | Aqueous sugar solution | NF membrane treatment | RO membrane treatment | Reagent grade monosaccharide |
|---|---|---|---|---|
| L-Lactic acid (Reference Example 8) | 5 g/L | 12 g/L | 11 g/L | 14 g/L |
| L-Lactic acid (Reference Example 9) | 5 g/L | 8 g/L | 7 g/L | 9 g/L |
| Ethanol (Reference Example 10) | 22 g/L | 29 g/L | 28 g/L | 29 g/L |
| Cadaverine (Reference Example 11) | 0.4 g/L | 1.1 g/L | 1.0 g/L | 1.3 g/L |
| D-Lactic acid (Reference Example 12) | 1.2 g/L | 7 g/L | 5 g/L | 9 g/L |
| Succinic acid (Reference Example 13) | 30 g/L | 35 g/L | 35 g/L | 35 g/L |

In terms of the L-lactic acid fermentation test using yeast (Reference Example 8), the amount of glucose in the sugar liquid consumed during the fermentation and the yield relative to the sugar (glucose) are shown in Table 40. The treatment of the aqueous sugar solution through the nanofiltration membrane or the reverse osmosis membrane resulted in better tendencies of improvement also in the consumption of the sugar, compared to the case in which the treatment was not carried out.

TABLE 40

Glucose consumption, and yield relative to sugar in L-lactic acid fermentation

| | Aqueous sugar solution | NF membrane treatment | RO membrane treatment | Reagent grade monosaccharide |
|---|---|---|---|---|
| Glucose consumption | 31 g/L | 48 g/L | 48 g/L | 49 g/L |
| Yields relative to the sugar (glucose) | 16% | 25% | 24% | 28% |

Example 18: Fermentation for Producing Chemical Products Using Sugar Liquids Purified from Hydrothermally Treated/Enzyme-Treated Aqueous Sugar Solution From about 1 liter each of the aqueous sugar solution and the purified sugar liquids (nanofiltration membrane-treated liquid and reverse osmosis membrane-treated liquid) in Example 2, water was evaporated under reduced pressure (200 hPa) using a rotary evaporator (manufactured by Tokyo Rikakikai) to obtain an about 1.2-fold concentrated solution/liquid. Using these and, for comparison, reagent grade glucose, medium components suitable for the respective cases of fermentation under the concentration conditions of the respective medium components described in the fermentation conditions shown in Reference Examples 8 to 13 were prepared, and the prepared medium components were used in the main culture. In the preculture, reagent grade glucose was used, and each sugar liquid was used only in the main culture. As a result, as shown in Table 41, the cases in which the membrane treatment was carried out showed better suppression of fermentation inhibition and improved concentrations of chemical products accumulated, compared to the case in which membrane treatment was not carried out.

TABLE 41

Concentrations of chemical products accumulated

| | Aqueous sugar solution | NF membrane treatment | RO membrane treatment | Reagent grade monosaccharide |
|---|---|---|---|---|
| L-Lactic acid (Reference Example 8) | 7 g/L | 14 g/L | 13 g/L | 14 g/L |
| L-Lactic acid (Reference Example 9) | 7 g/L | 9 g/L | 8 g/L | 9 g/L |
| Ethanol (Reference Example 10) | 25 g/L | 29 g/L | 29 g/L | 29 g/L |
| Cadaverine (Reference Example 11) | 0.7 g/L | 1.3 g/L | 1.2 g/L | 1.3 g/L |
| D-Lactic acid (Reference Example 12) | 2.8 g/L | 8 g/L | 7 g/L | 9 g/L |
| Succinic acid (Reference Example 13) | 32 g/L | 35 g/L | 35 g/L | 35 g/L |

Example 19: Fermentation for Producing Chemical Products Using Sugar Liquids Purified from Ammonia-Treated/Enzyme-Treated Aqueous Sugar Solution From about 1 liter each of the aqueous sugar solution and the purified sugar liquids (nanofiltration membrane-treated liquid and reverse osmosis membrane-treated liquid) in Example 3, water was evaporated under reduced pressure (200 hPa) using a rotary evaporator (manufactured by Tokyo Rikakikai) to obtain an about 1.2-fold concentrated solution/liquid. Using these and, for comparison, reagent grade glucose, medium components suitable for the respective cases of fermentation under the concentration conditions of the respective medium components described in the fermentation conditions shown in Reference Examples 8 to 13 were prepared, and the prepared medium components were used in the main culture. In the preculture, reagent grade glucose was used, and each sugar liquid was used only in the main culture. As a result, as shown in Table 42, the cases in which the membrane treatment was carried out showed better suppression of fermentation inhibition and improved concentrations of chemical products accumulated, compared to the case in which the treatment was not carried out.

TABLE 42

Concentrations of chemical products accumulated

|  | Aqueous sugar solution | NF membrane treatment | RO membrane treatment | Reagent grade monosaccharide |
|---|---|---|---|---|
| L-Lactic acid (Reference Example 8) | 6 g/L | 13 g/L | 11 g/L | 14 g/L |
| L-Lactic acid (Reference Example 9) | 6 g/L | 9 g/L | 7 g/L | 9 g/L |
| Ethanol (Reference Example 10) | 23 g/L | 29 g/L | 29 g/L | 29 g/L |
| Cadaverine (Reference Example 11) | 0.6 g/L | 1.2 g/L | 1.1 g/L | 1.3 g/L |
| D-Lactic acid (Reference Example 12) | 2.1 g/L | 8 g/L | 6 g/L | 9 g/L |
| Succinic acid (Reference Example 13) | 31 g/L | 35 g/L | 35 g/L | 35 g/L |

Example 20: Fermentation for Producing Chemical Products Using Sugar Liquids Purified from Hydrothermally Treated Aqueous Sugar Solution From 1 liter each of the aqueous sugar solution and the purified sugar liquids (NF membrane-treated liquid and RO membrane-treated liquid) in Example 5, water was evaporated under reduced pressure (200 hPa) using a rotary evaporator (manufactured by Tokyo Rikakikai) to obtain an about 20-fold concentrated solution/liquid. Using these and, for comparison, reagent grade glucose, medium components suitable for the respective cases of fermentation under the concentration conditions of the respective medium components described in the fermentation conditions shown in Reference Examples 8 to 13 were prepared, and the prepared medium components were used in the main culture. In the preculture, reagent grade glucose was used, and each sugar liquid was used only in the main culture. As a result, as shown in Table 43, the cases in which the membrane treatment was carried out showed better suppression of fermentation inhibition and improved concentrations of chemical products accumulated, compared to the case in which the treatment was not carried out.

TABLE 43

Concentrations of chemical products accumulated

|  | Aqueous sugar solution | NF membrane treatment | RO membrane treatment | Reagent grade monosaccharide |
|---|---|---|---|---|
| L-Lactic acid (Reference Example 8) | 0 g/L | 9 g/L | 4 g/L | 14 g/L |
| L-Lactic acid (Reference Example 9) | 0 g/L | 6 g/L | 3 g/L | 9 g/L |
| Ethanol (Reference Example 10) | 12 g/L | 24 g/L | 14 g/L | 29 g/L |
| Cadaverine (Reference Example 11) | 0 g/L | 0.5 g/L | 0 g/L | 1.3 g/L |
| D-Lactic acid (Reference Example 12) | 0 g/L | 9 g/L | 0 g/L | 9 g/L |
| Succinic acid | 21 g/L | 32 g/L | 26 g/L | 35 g/L |

Example 21: Effect of pH of Aqueous Sugar Solution on Production of Chemical Products To investigate the effect of the pH of the aqueous sugar solution on production of chemical products using the purified sugar liquid, results of L-lactic acid fermentation using aqueous sugar solutions having different pHs were compared and studied. As carbon sources of fermentation media, the two types of purified sugar liquids in Example 7 (prepared by treating aqueous sugar solutions at pHs of 3 and 7 through a reverse osmosis membrane) were used, and, as a control, reagent grade glucose was used. With sulfuric acid and aqueous ammonia, 0.5 L each of the purified sugar liquids in Example 7 was adjusted to pH 5, and the resulting liquids were diluted to a glucose concentration of 55 g/L, to provide the sugar liquids A and B (A: treated through a reverse osmosis membrane at pH 3; B: treated through a reverse osmosis membrane at pH 7). To these sugar liquids, Yeast Synthetic Drop-out Medium Supplement Without Tryptophan (Sigma Aldrich Japan, Table 34, Drop-out MX), Yeast Nitrogen Base w/o Amino Acids and Ammonium Sulfate (Difco, Yeast NTbase), and ammonium sulfate were blended such that the ratio shown in Table 34 for the L-lactic acid fermentation medium in Reference Example 8 was attained, to provide the purified sugar liquid A and B media, respectively. Similarly, a reagent grade monosaccharide medium was prepared by blending of reagent grade glucose at the ratio shown in Table 34.

Each medium was subjected to sterilization by filtration (Millipore, Stericup 0.22 μm) before being used in the fermentation. The concentration of glucose was quantified using Glucose Test Wako (manufactured by Wako Pure Chemical Industries, Ltd.). The amount of lactic acid produced in each culture was measured by HPLC under the same conditions as in the measurement of organic acids by HPLC in Reference Example 2.

In accordance with the method in Reference Example 8, the yeast SW-1 strain was precultured in 5 mL of the reagent grade monosaccharide medium in a test tube, and main culture was then carried out in the purified sugar liquid A and B media and the reagent grade monosaccharide medium. As a result, as shown in Table 44, use of the purified sugar liquid prepared by treating the aqueous sugar solution (pH 3) through a reverse osmosis membrane resulted in a higher consumption, which was equivalent to the consumption observed in case of the reagent grade monosaccharide medium, of glucose by the microorganism compared to the case of the purified sugar liquid prepared by treating the aqueous sugar solution (pH 7) through a reverse osmosis membrane. Thus, it could be confirmed that fermentation inhibition was reduced in the former case. Further, it was also shown that the concentration of accumulated lactic acid in the case of the purified sugar liquid medium prepared by filtering the aqueous sugar solution (pH 3) through a reverse osmosis membrane was equivalent to that in the case of the reagent grade monosaccharide medium.

TABLE 44

Results of L-lactic acid fermentation (after 24 hours of culture)

| | Glucose consumption | Concentration of lactic acid accumulated | Yield relative to sugar (glucose) |
|---|---|---|---|
| Purified sugar liquid A medium | 50 g/L | 14 g/L | 28% |
| Purified sugar liquid B medium | 40 g/L | 10 g/L | 25% |
| Reagent grade monosaccharide medium | 50 g/L | 14 g/L | 28% |

Example 22: Comparison of Performances of Nanofiltration Membrane and Reverse Osmosis Membrane in Production of Chemical Products To compare performances of the nanofiltration membrane and the reverse osmosis membrane in production of chemical products, results of ethanol fermentation were compared and studied among the sugar liquid prepared by purification through the nanofiltration membrane, the sugar liquid prepared by purification through the reverse osmosis membrane and the sugar liquid prepared by purification through the nanofiltration membrane and the reverse osmosis membrane. As carbon sources, the three types of purified sugar liquids in Example 15 (those subjected to nanofiltration membrane treatment, reverse osmosis membrane treatment, or nanofiltration membrane treatment followed by reverse osmosis membrane treatment) were used, and, as a control, reagent grade glucose was used. With aqueous ammonia, 0.5 L each of the concentrated sugar liquids obtained in Example 15 was adjusted to pH 5, and the resulting liquids were diluted to a glucose concentration of 55 g/L, to provide the sugar liquids E, F and G (E: treated through a nanofiltration membrane; F: treated through a nanofiltration membrane and then through a reverse osmosis membrane; G: treated through a reverse osmosis membrane). To these sugar liquids, Yeast Synthetic Drop-out Medium Supplement Without Tryptophan (Sigma Aldrich Japan, Table 34, Drop-out MX), Yeast Nitrogen Base w/o Amino Acids and Ammonium Sulfate (Difco, Yeast NTbase), and ammonium sulfate were blended such that the ratio shown in Table 34 in Reference Example 8 was attained, to provide the purified sugar liquid C to E media, respectively. Similarly, a reagent grade monosaccharide medium was prepared by blending of reagent grade glucose at the ratio shown in Table 34.

Each medium was subjected to sterilization by filtration (Millipore, Stericup 0.22 μm) before being used in the fermentation. The concentration of glucose was quantified using Glucose Test Wako (manufactured by Wako Pure Chemical Industries, Ltd.). The amount of ethanol produced in each culture was measured by GC under the conditions described in Reference Example 1.

In accordance with the method in Reference Example 9, the OC2 strain was precultured in 5 mL of the reagent grade monosaccharide medium in a test tube, and main culture was then carried out in the purified sugar liquid C to E media and the reagent grade monosaccharide medium. As a result, as shown in Table 45, C and D, in which the sugar liquids purified with the nanofiltration membrane were used, showed amounts of glucose consumption and concentrations of accumulated ethanol equivalent to those in the case of the reagent grade monosaccharide medium. Thus, it could be confirmed that fermentation inhibition was reduced in these cases. E, in which the sugar liquid purified with the reverse osmosis membrane was used, was also confirmed to show fermentation almost equivalent to that in the case of the reagent grade monosaccharide medium, although slightly worse than C and D.

TABLE 45

Results of ethanol fermentation (after 48 hours of culture)

| | Glucose consumption | Concentration of ethanol accumulated |
|---|---|---|
| Purified sugar liquid C medium | 50 g/L | 29 g/L |
| Purified sugar liquid D medium | 50 g/L | 29 g/L |
| Purified sugar liquid E medium | 48 g/L | 27 g/L |
| Reagent grade monosaccharide medium | 50 g/L | 29 g/L |

Reference Example 14: Preparation of *E. coli* for Cadaverine Fermentation

To enhance the expression level of the lysine decarboxylase gene existing in the *E. coli* chromosome to increase the cadaverine fermentation performance, preparation of a strain in which the promoter of the lysine decarboxylase gene is replaced with the promoter of the gapA gene (glyceraldehyde dehydrogenase gene) of *E. coli* was attempted. The replacement of the promoter was carried out by a modified method of gene disruption by homologous recombination using FLP recombinase. The method of preparation was as follows.

<1> Cloning of gapA Gene Promoter

The *E. coli* W3110 strain was cultured and collected by centrifugation, and its genomic DNA was extracted using UltraClean Microbial DNA Isolation Kit (manufactured by MO BIO Laboratories, Inc.). For details of the operation, the manufacturer's instructions were followed.

Using the thus obtained genomic DNA as a template and oligonucleotides (SEQ ID NO:10 (KS029) and SEQ ID NO:11 (KS030)) as a primer set, PCR was carried out to amplify the gapA gene promoter (500 bp in the upstream of the gapA gene; hereinafter referred to as "gapA promoter"). For the PCR amplification reaction, KOD-Plus polymerase (manufactured by Toyobo Co. Ltd.) was used, and the reaction buffer and the dNTP mix attached to the polymerase were used. Fifty microliters of a reaction system was prepared such that 50 ng/sample of the genomic DNA prepared as described above in accordance with the manufacturer's instructions attached to the polymerase, 50 pmol/sample of the primers and 1 unit/sample of KOD-Plus polymerase (manufactured by Toyobo Co. Ltd.) were contained therein. The reaction solution was subjected to heat denaturation using a PCR amplification device iCycler (manufactured by BIO-RAD) at 94° C. for 5 minutes; followed by 30 cycles of: 94° C. for 30 seconds (heat denaturation), 55° C. for 30 seconds (annealing of the primers) and 68° C. for 30 seconds (extension of the complementary strand); and the solution was then cooled to a temperature of 4° C. The gene amplification primers (SEQ ID NO:10 (KS029) and SEQ ID NO:11 (KS030)) were prepared such that the sequence recognized by HindIII is attached to their 5'-ends and the 3'-ends.

Each PCR-amplified fragment was phosphorylated at its ends with T4 Polynucleotide Kinase (manufactured by TAKARA BIO INC.), followed by ligation into pUC118 vector (which had been digested with the restriction enzyme HincII and dephosphorylated at the site of cleavage). The ligation was carried out using DNA Ligation Kit Ver. 2 (manufactured by TAKARA BIO INC.). *E. coli* DH5α competent cells (manufactured by TAKARA BIO INC.) were transformed with the ligation solution, and plated on an LB plate supplemented with 50 µg/L ampicillin, which is an antibiotic, followed by culturing the cells overnight. Plasmid DNAs were recovered from grown colonies by miniprep, and cleaved with the restriction enzyme HindIII, followed by selecting plasmids in which the gapA promoter is inserted. The entire series of operations were carried out in accordance with the attached manufacturer's instructions.

<2> Cloning of Lysine Decarboxylase Gene

Subsequently, PCR was carried out using the genomic DNA of *E. coli* W3110 obtained in <1> as a template and oligonucleotides (SEQ ID NO:12 (CadAF2) and SEQ ID NO:13 (CadAR2)) as a primer set, to carry out cloning of the cadA gene encoding lysine decarboxylase. The PCR amplification reaction was carried out under the same conditions as in <1> except that the extension reaction was carried out for 2 minutes. The gene amplification primers (SEQ ID NO:12 (CadAF2) and SEQ ID NO:13 (CadAR2)) were prepared such that the sequence recognized by HindIII is attached to their 5'-ends and the sequence recognized by XbaI is attached to their the 3'-ends. The obtained DNA fragment was ligated into pUC118 vector in the same manner as in <1>, to obtain pUC118 vector in which the cadA gene is inserted. The obtained vector was cleaved with HindIII and XbaI to confirm insertion of the cadA gene in the plasmid.

Subsequently, this pUC118 vector in which the cadA gene is inserted was cleaved with the restriction enzymes HindIII and XbaI, and the obtained DNA fragment containing the cadA gene was ligated into the HindIII XbaI cleavage site of pUC19. The obtained plasmid DNA was recovered and cleaved with the restriction enzymes HindIII and XbaI, thereby selecting an expression vector in which the cadA gene is inserted. The obtained plasmid was designated pHS7.

<3> Cloning of Chloramphenicol Resistance Gene

The cat gene was cloned by PCR using, as a template, the vector pKD3 having the chloramphenicol resistance gene (cat gene) and FLP recognition sites in the upstream and downstream thereof, and, as a primer set, oligonucleotides (SEQ ID NO:14 and SEQ ID NO:15). The PCR amplification reaction was carried out under the same conditions as in <1> except that the extension reaction was carried out for 1 minute. The gene amplification primers (SEQ ID NO:14 and SEQ ID NO:15) were prepared such that the sequence recognized by BamHI is attached to their 5'-ends and the sequence recognized by SacI is attached to their the 3'-ends. The obtained DNA fragment was ligated into pUC118 vector in the same manner as in <1>, to obtain pUC118 vector in which the cat gene is inserted. The obtained vector was cleaved with the restriction enzymes BamHI and SacI to confirm insertion of the cat gene in the plasmid.

<4> Insertion of Cat Gene and gapA Promoter into pHS7

Subsequently, the pUC118 vector in which the cat gene was inserted was cleaved with the restriction enzyme BamHI, and a plasmid was prepared by introducing the obtained DNA fragment to the BamHI/SacI cleavage site of the above-described pHS7. The obtained vector was cleaved with the restriction enzymes BamHI and SacI to confirm insertion of the cat gene in the plasmid. The thus obtained plasmid was designated pKS5.

<5> Introduction of gapA Promoter-cadA Gene Cassette to Chromosome

Subsequently, the pUC118 vector in which the gapA promoter is inserted was cleaved with the restriction enzyme HindIII, and a plasmid was prepared by introducing the obtained DNA fragment to the HindIII cleavage site of the above-described pKS5. PCR was carried out using this plasmid DNA as a template, and oligonucleotides (SEQ ID NO:16 (M13 RV) and SEQ ID NO:11 (KS030)) as a primer set. For the PCR, PremixTaq ExTaq Ver (manufactured by TAKARA BIO INC.) was used. By this PCR, a plasmid from which an amplified fragment of about 500 bp can be obtained was selected as the plasmid of interest. The thus obtained plasmid was designated pKS8.

Using, as a template, pKS8 obtained as described in <4>, and, as a primer set, oligonucleotides (SEQ ID NO:17 (KS032) and SEQ ID NO:18 (KS033)), PCR was carried out to amplify a DNA fragment containing the gapA promoter, the cadA gene and the cat gene. For the PCR amplification reaction, KOD-Plus polymerase (manufactured by Toyobo Co. Ltd.) was used, and the reaction buffer and the dNTP mix attached to the polymerase were used. Fifty microliters of a reaction system was prepared such that 50 ng/sample of the plasmid DNA, 50 pmol/sample of the primers and 1 unit/sample of KOD-Plus polymerase (manufactured by Toyobo Co. Ltd.) were contained therein. The reaction solution was subjected to heat denaturation using a PCR amplification device iCycler (manufactured by BIO-RAD) at 94° C. for 5 minutes; followed by 30 cycles of: 94° C. for 30 seconds (heat denaturation), 65° C. for 30 seconds (annealing of the primers) and 68° C. for 3 minutes and 30 seconds (extension of the complementary strand); and the solution was then cooled to a temperature of 4° C. The obtained amplified fragment of about 3.5 kb was extracted from the agarose gel after electrophoresis according to a conventional method, and the concentration was adjusted to 500 ng/µL.

A strain (hereinafter referred to as W3110/pKD46) prepared by introducing the plasmid pKD46 having FLP recombinase to the W3110 strain was inoculated in 5 mL of LB medium, and cultured overnight at 30° C. (preculture). The obtained preculture was subjected to 1% inoculation to 5 mL of SOB medium (supplemented with 1 mM arabinose), followed by culturing at 30° C. until an $OD_{600}$ of 0.6 is attained (main culture). The main culture was centrifuged to collect the bacterial cells, and the bacterial cells were washed 3 times with ice-cooled 10% glycerol, followed by finally suspending the bacterial cells in 50 µL of 10% glycerol. To this bacterial cell suspension, 2 µL of the PCR-amplified fragment purified as described above was added, and the resulting mixture was cooled on ice for 30 minutes. This suspension was transferred to an electroporation cuvette (0.2 cm), and electroporation was carried out (2500 V, 25 µF, 200Ω) using GenePulser Xcell (manufactured by BIO-RAD). After applying an electric pulse, 1 mL of SOC medium was fed to the cuvette, and the bacterial cell suspension was collected, followed by culturing at 37° C. for 2.5 hours. The culture was applied to LB agar medium supplemented with 25 μg/L chloramphenicol, and cultured at 37° C. overnight.

After confirming that the obtained colony did not grow in LB medium supplemented with ampicillin, confirmation of the fact that it is the strain of interest in which the promoter of the cadA gene is replaced with the gapA promoter was carried out by PCR using the extracted genome as a template and oligonucleotides (SEQ ID NO:19 (KS007) and SEQ ID NO:20 (KS008)) as primers. In the strain of interest produced by homologous recombination, an amplified product of about 3.8 kb is obtained, while in a strain in which the insertion by homologous recombination did not occur at the position of interest, an amplified product of about 2.3 kb is obtained. As a result, the amplified product of about 3.8 kb could be confirmed. This strain, in which the promoter of the cadA gene is replaced with the gapA promoter, was designated the W3110(gapA-cadA) strain.

Example 23: Production of Purified Sugar Liquid Containing Xylose Component

As sugar liquids containing large amounts of the xylose component, the dilute sulfuric acid-treated liquid in Reference Example 3 (xylose concentration, 15 g/L) and the hydrothermally treated liquid in Reference Example 4 (xylose concentration, 14 g/L) were adjusted to pH 3 and pH 7 with an aqueous calcium hydroxide solution and sulfuric acid, respectively, followed by filtering the resulting liquids through a microfiltration membrane. The turbidity of each liquid was not more than 1.0 NTU at this time. These aqueous sugar solutions, a total of 4 types, were treated through a nanofiltration membrane by the same method as in Example 1, to obtain purified sugar liquids. Using, as the nanofiltration membrane, a cross-linked piperazine polyamide nanofiltration membrane UTC60 (nanofiltration membrane 1; manufactured by TORAY INDUSTRIES, INC.), filtration was carried out until the volume of the raw liquid decreased to one fourth of the initial volume. The concentrations of fermentation-inhibiting substances and monosaccharides contained in each concentrate in the raw liquid tank at this time were analyzed by HPLC (manufactured by Shimadzu Corporation). The results obtained for the fermentation-inhibiting substances (acetic acid, formic acid, HMF, furfural, vanillin, acetovanillin and syringic acid) and monosaccharides (glucose and xylose) were as shown in Tables 46 and 47.

TABLE 46

Fermentation-inhibiting substances contained in purified sugar liquid containing large amount of xylose component

| | Dilute-sulfuric-acid treatment liquid | Sugar liquid purified from dilute-sulfuric-acid treatment liquid (pH 3) | Sugar liquid purified from dilute-sulfuric-acid treatment liquid (pH 7) | Hydrothermally treated liquid | Sugar liquid purified from hydrothermally treated liquid (pH 3) | Sugar liquid purified from hydrothermally treated liquid (pH 7) |
|---|---|---|---|---|---|---|
| Acetic acid | 2.0 g/L | 1.8 g/L | 7.9 g/L | 2.2 g/L | 2.0 g/L | 8.6 g/L |
| Formic acid | 0.1 g/L | 0.08 g/L | 0.3 g/L | 0.5 g/L | 0.4 g/L | 1.8 g/L |
| Furfural | 560 mg/L | 560 mg/L | 560 mg/L | 8 mg/L | 8 mg/L | 8 mg/L |
| HMF | 100 mg/L | 100 mg/L | 100 mg/L | 139 mg/L | 139 mg/L | 139 mg/L |
| Vanillin | 60 mg/L | 63 mg/L | 63 mg/L | 50 mg/L | 52 mg/L | 52 mg/L |
| Acetovanillin | 120 mg/L | 130 mg/L | 130 mg/L | 2 mg/L | 2.3 mg/L | 2.3 mg/L |
| Syringic acid | 10 mg/L | 12 mg/L | 12 mg/L | 1 mg/L | 1.2 mg/L | 1.2 mg/L |

TABLE 47

Monosaccharide composition of purified sugar liquid containing large amount of xylose component

| | Dilute-sulfuric-acid treatment liquid, before NF membrane-treatment | Dilute-sulfuric-acid treatment liquid, after NF membrane-treatment (pH 3) | Dilute-sulfuric-acid treatment liquid, after NF membrane-treatment (pH 7) | Hydrothermally treated liquid, before NF membrane-treatment | Hydrothermally treated liquid, after NF membrane-treatment (pH 3) | Hydrothermally treated liquid, after NF membrane-treatment (pH 7) |
|---|---|---|---|---|---|---|
| Glucose | 3 g/L | 12 g/L | 12 g/L | 2 g/L | 8 g/L | 8 g/L |
| Xylose | 15 g/L | 59 g/L | 59 g/L | 14 g/L | 56 g/L | 56 g/L |
| Arabinose | 0.8 g/L | 3.2 g/L | 3.2 g/L | 0.5 g/L | 2.0 g/L | 2.0 g/L |
| Mannose | 0.9 g/L | 3.6 g/L | 3.6 g/L | 0.5 g/L | 2.0 g/L | 2.0 g/L |

Example 24: Cadaverine Fermentation by *E. coli* Using Xylose Sugar Liquid

A cadaverine fermentation test by the cadaverine fermentation *E. coli* strain in Reference Example 14 (W3110(gapA-cadA) strain) was carried out. In terms of the media, a total of 5 types of carbon sources, that is, the 4 types of purified sugar liquids in Example 23 and, for comparison, reagent grade monosaccharide prepared using reagent grade glucose and xylose, were used. With sulfuric acid and aqueous ammonia, 0.5 L each of the purified sugar liquids was adjusted to pH 5, to provide the sugar liquids F, G, H and I (F: prepared by treating the hydrothermally treated liquid through a nanofiltration membrane at pH 3; G: prepared by treating the hydrothermally treated liquid through a nanofiltration membrane at pH 7; H: prepared by treating the dilute sulfuric acid-treated liquid through a nanofiltration membrane at pH 3; I: prepared by treating the dilute sulfuric acid-treated liquid through a nanofiltration membrane at pH 7). To these sugar liquids, magnesium sulfate, ammonium sulfate, potassium dihydrogen phosphate and polypeptone S were blended at the ratio shown in Table 48, to provide the purified sugar liquid F to I media, respectively. The reagent grade monosaccharide medium was prepared by blending the above components at the ratio shown in Table 48 such that the concentration of reagent grade xylose is 50 g/L. Each medium was subjected to sterilization by filtration (Millipore, Stericup 0.22 μm) before being used in the fermentation. The concentration of xylose was quantified using a xylose concentration measurement kit (Megazyme).

TABLE 48

Composition of medium for cadaverine fermentation by *E. coli*

| Composition | Concentration of component |
| --- | --- |
| Xylose | 50 g/L |
| Magnesium sulfate | 1 g/L |
| Ammonium sulfate | 16 g/L |
| Potassium dihydrogenphosphate | 1 g/L |
| Polypeptone S | 10 g/L |

The W3110(gapA-cadA) strain was cultured in 5 mL of the reagent grade monosaccharide medium in a test tube with shaking overnight (preculture). The bacterial cells were collected from the preculture by centrifugation, and washed well with 15 mL of sterile water. The washed bacterial cells were inoculated to 100 mL each of the media described in Table 48, and cultured in a 500-mL Sakaguchi flask for 24 hours with shaking. As a result, as shown in Table 49, use of the purified sugar liquids F and H treated through a nanofiltration membrane at pH 3 resulted in higher consumptions of xylose, compared to the cases of the purified sugar liquids G and I treated through a nanofiltration membrane at pH 7. Thus, it could be confirmed that fermentation inhibition was reduced in the former cases. Further, it was shown that the concentration of accumulated cadaverine was also equivalent to that in the case of the reagent grade monosaccharide medium.

TABLE 49

Results of cadaverine fermentation (after 48 hours of culture)

|  | Xylose consumption | Concentration of cadaverine accumulated |
| --- | --- | --- |
| Purified sugar liquid F medium | 47.5 g/L | 1.0 g/L |
| Purified sugar liquid G medium | 1.2 g/L | 0.0 g/L |
| Purified sugar liquid H medium | 44.0 g/L | 1.0 g/L |
| Purified sugar liquid I medium | 24.5 g/L | 0.6 g/L |
| Reagent grade monosaccharide medium | 48.5 g/L | 1.0 g/L |

INDUSTRIAL APPLICABILITY

Fermentation-inhibiting substances can be removed from an aqueous sugar solution derived from a cellulose-containing biomass, and, on the other hand, a purified sugar liquid containing monosaccharides such as glucose and xylose can be produced at high purity and at high yield so that use of the purified sugar liquid as a fermentation feedstock enables enhancement of the efficiencies of fermentative production of various chemical products.

DESCRIPTION OF SYMBOLS

1. Raw liquid tank
2. Cell equipped with nanofiltration membrane or reverse osmosis membrane
3. High-pressure pump
4. Flow of liquid which has permeated through membrane
5. Flow of liquid which has been concentrated with membrane
6. Flow of culture sent by high-pressure pump, or permeate from nanofiltration membrane
7. Nanofiltration membrane or reverse osmosis membrane
8. Supporting plate

The invention claimed is:

1. A method of producing a sugar liquid using a cellulose-containing biomass as a raw material comprising:
   (a) hydrolyzing a cellulose-containing biomass to produce an aqueous sugar solution; and
   (b) filtering the obtained aqueous sugar solution through a reverse osmosis membrane to collect a purified sugar liquid from a feed side, while removing fermentation-inhibiting substances comprising vanillin from a permeate side,
      wherein (b) filters said aqueous sugar solution through a nanofiltration membrane to collect a purified sugar liquid from a feed side and filters obtained filtrate through the reverse osmosis membrane to recover sugar from said obtained filtrate at a feed side, and
      wherein the reverse osmosis membrane is selected from a cross-linked wholly aromatic polyamide reverse osmosis membrane and a polyamide reverse osmosis membrane.

2. The method according to claim 1, wherein pH of said aqueous sugar solution in (b) is adjusted to 1 to 5.

3. The method according to claim 1, wherein pH of said aqueous sugar solution in (b) is adjusted to 1 to 3.

4. The method according to claim 1, wherein said purified sugar liquid in (b) is a sugar liquid containing a monosaccharide as a major component.

5. The method according to claim 1, wherein said aqueous sugar solution obtained in (a) is further filtered through a microfiltration membrane and/or ultrafiltration membrane to remove fine particles and macromolecular components before treatment of (b).

6. The method according to claim 1, wherein temperature of said aqueous sugar solution in (b) is adjusted to 1 to 15° C. and the solution is further filtered through a nanofiltration membrane.

7. The method according to claim 1, wherein temperature of said aqueous sugar solution in (b) is adjusted to 40° C. to 80° C.

8. The method according to claim 1, wherein functional layer(s) of said reverse osmosis membrane in (b) is/are polyamide.

9. The method according to claim 1, wherein functional layer(s) of said reverse osmosis membrane in (b) is/are cellulose acetate.

10. A method of producing a chemical product comprising obtaining a sugar liquid by the method according to claim 1; and culturing a microorganism or cultured cell with the sugar liquid as a fermentation feedstock.

11. The method according to claim 2, wherein said fermentation-inhibiting substances comprise one or more selected from the group consisting of organic acids, furan compounds and phenolic compounds.

12. The method according to claim 2, wherein said purified sugar liquid in (2) is a sugar liquid containing a monosaccharide as a major component.

13. A method of producing a sugar liquid using a cellulose-containing biomass as a raw material comprising:
   (a) hydrolyzing a cellulose-containing biomass to produce an aqueous sugar solution; and
   (b) filtering the obtained aqueous sugar solution through a reverse osmosis membrane to collect a purified sugar liquid from a feed side, while removing fermentation-inhibiting substances comprising vanillin from a permeate side,
      wherein (b) filters said aqueous sugar solution through a nanofiltration membrane to collect a purified sugar liquid from a feed side and filtering obtained filtrate through the reverse osmosis membrane to recover sugar from said obtained filtrate at a feed side, and
      wherein the reverse osmosis membrane is selected from a cross-linked wholly aromatic polyamide reverse osmosis membrane, a polyamide reverse osmosis membrane and a cellulose acetate reverse osmosis membrane.

* * * * *